(12) United States Patent
Caplan et al.

(10) Patent No.: US 11,377,656 B2
(45) Date of Patent: Jul. 5, 2022

(54) CHEMICALLY MODIFIED MESSENGER RNA'S

(71) Applicant: Novartis AG, Basel (CH)

(72) Inventors: Shari Lynn Caplan, Lunenburg, MA (US); Katsumasa Nakajima, Winchester, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/083,327

(22) PCT Filed: Mar. 8, 2017

(86) PCT No.: PCT/IB2017/051367
§ 371 (c)(1),
(2) Date: Sep. 7, 2018

(87) PCT Pub. No.: WO2017/153936
PCT Pub. Date: Sep. 14, 2017

(65) Prior Publication Data
US 2019/0100752 A1    Apr. 4, 2019

Related U.S. Application Data

(60) Provisional application No. 62/306,384, filed on Mar. 10, 2016.

(51) Int. Cl.
*C07H 21/04* (2006.01)
*C12N 15/11* (2006.01)
*C07H 21/02* (2006.01)
*C12N 15/87* (2006.01)

(52) U.S. Cl.
CPC ............. *C12N 15/11* (2013.01); *C07H 21/02* (2013.01); *C12N 15/87* (2013.01)

(58) Field of Classification Search
None
See application file for complete search history.

(56) References Cited

U.S. PATENT DOCUMENTS 9,750,824 B2 * 9/2017 Kariko .................... C12Q 1/68

FOREIGN PATENT DOCUMENTS

WO    2015/196128 A2    12/2015

OTHER PUBLICATIONS

Cantara, William A., et al. "The RNA modification database, RNAMDB: 2011 update." Nucleic acids research 39.suppl_1 (2010): D195-D201.*
International Search Report and Written Opinion for International Application No. PCT/IB2017/051367 dated May 29, 2017. 12 pages.

* cited by examiner

*Primary Examiner* — Kimberly Chong
(74) *Attorney, Agent, or Firm* — Linyu L. Mitra

(57) ABSTRACT

This invention provides messenger RNA (mRNA) molecules comprising an open reading frame that encodes a protein of interest, wherein said modified RNA comprises a modified nucleoside selected from the group consisting of: (I), (II), and (III), gene therapy vectors comprising same, methods of synthesizing same, and methods for gene replacement, gene therapy, gene transcription silencing, and the delivery of therapeutic proteins to tissue in vivo, comprising the molecules. The present invention also provides methods of reducing the immunogenicity of mRNA molecules.

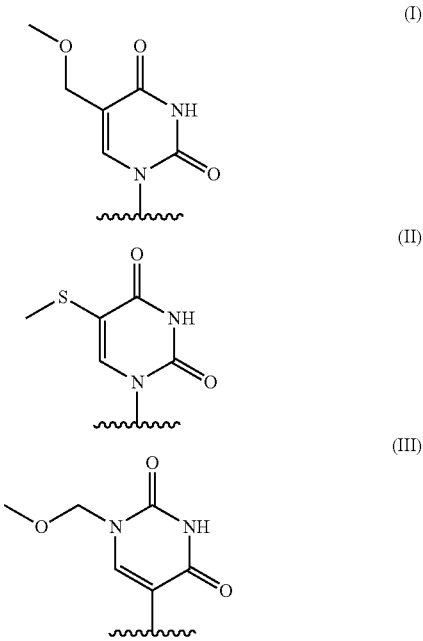

8 Claims, No Drawings

CHEMICALLY MODIFIED MESSENGER RNA'S

CROSS-REFERENCE TO RELATED APPLICATIONS

This application is a 371 Application of PCT Application No. PCT/IB2017/051367, filed Mar. 8, 2017, which claims priority to U.S. Patent Application No. 62/306,384, filed Mar. 10, 2016, the contents of each of which are incorporated herein by reference in their entireties.

FIELD OF INVENTION

This invention provides modified messenger RNA molecules (mRNA's) comprising a modified nucleoside, gene therapy vectors comprising same, methods of synthesizing same, and methods for gene replacement, gene therapy, gene transcription silencing, and the delivery of therapeutic proteins to tissue in vivo, comprising the molecules. The present invention also provides methods of reducing the immunogenicity of messenger RNA molecules.

BACKGROUND OF THE INVENTION

All naturally occurring RNA is synthesized from four basic ribonucleotides ATP, CTP, UTP and GTP, but some of the incorporated nucleosides are modified post-transcriptionally in ribosomal RNA or transfer RNA. Nearly one hundred different nucleoside modifications have been identified in RNA (Rozenski, J, Crain, P, and McCloskey, J. (1999). The RNA Modification Database: 1999 update. Nucl Acids Res 27: 196-197). The extent and nature of modifications vary and depend on the RNA type as well as the evolutionary level of the organism from where the RNA is derived. Bacterial messenger RNA (mRNA) contains no nucleoside modifications, while mammalian mRNA may contain post-transcriptionally modified nucleosides such as 5-methylcytosine ($m^5C$), N6-methyladenosine ($m^6A$), inosine (I) and 2'-O-methylated nucleosides, in addition to N7-methylguanosine ($m^7G$), which is part of the 5'-terminal cap. The role of nucleoside modifications on the immunostimulatory potential and on the translation efficiency of RNA, however, is not known.

There are multiple problems with prior methodologies of effecting protein expression. For example, heterologous DNA introduced into a cell can be inherited by daughter cells (whether or not the heterologous DNA has integrated into the chromosome) or by offspring. Introduced DNA can integrate into host cell genomic DNA at some frequency, resulting in alterations and/or damage to the host cell genomic DNA. In addition, multiple steps must occur before a protein is made. Once inside the cell, DNA must be transported into the nucleus where it is transcribed into RNA. The RNA transcribed from DNA must then enter the cytoplasm where it is translated into protein. This need for multiple processing steps creates lag times before the generation of a protein of interest. Further, it is difficult to obtain DNA expression in cells; frequently DNA enters cells but is not expressed or not expressed at reasonable rates or concentrations. This can be a particular problem when DNA is introduced into cells such as primary cells or modified cell lines.

There is a need in the art for biological modalities to address the modulation of intracellular translation of nucleic acids.

SUMMARY OF THE INVENTION

The present invention solves this problem by providing new mRNA molecules incorporating chemical alterations which impart properties which are advantageous to therapeutic development.

This invention provides a modified messenger RNA (mRNA) comprising an open reading frame that encodes a protein of interest, wherein said modified RNA comprises a modified nucleoside selected from the group consisting of:

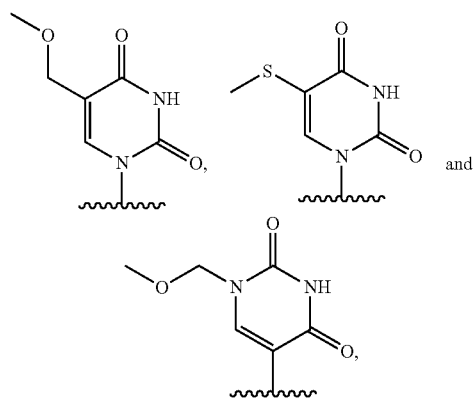

gene therapy vectors comprising same, gene therapy methods and gene transcription silencing methods comprising same, methods of reducing an immunogenicity of same, and methods of synthesizing same.

In another embodiment, the invention provides a method for inducing a mammalian cell to produce a protein of interest comprising the step of: repeatedly administering to said mammalian cell modified messenger RNA comprising an open reading frame that encodes a protein of interest, wherein said modified messenger RNA comprises at least one modified nucleoside selected from the group consisting of

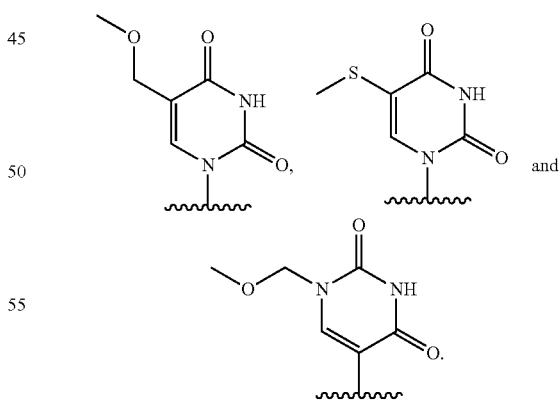

In yet another embodiment, the invention provides a method of treating a condition in a mammal caused by a deficiency of a protein of interest, comprising: administering a therapeutically effective amount of a modified messenger RNA comprising an open reading frame that encodes the protein of interest, wherein said modified RNA comprises a modified nucleoside selected from the group consisting of:

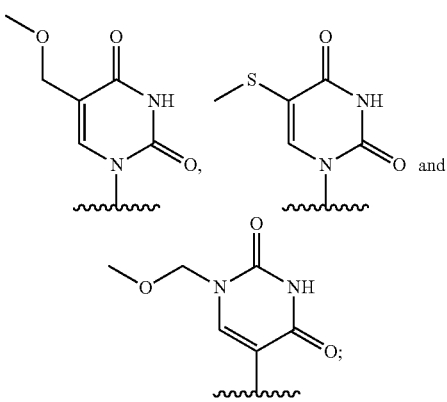

wherein said modified messenger RNA is taken up by a cell of said mammal, and said protein of interest is translated from said modified messenger RNA by said mammalian cell; thereby relieving said condition in said mammal.

DETAILED DESCRIPTION OF THE INVENTION

As used herein, the term "messenger RNA" includes self-amplifying messenger RNA ("SAM"), which replicate in host cells leading to an amplification of the amount of RNA encoding a desired gene product, and which can enhance efficiency of RNA delivery and expression of the encoded gene products. See, WO 2011/005799 A2 (Novartis AG); Brito L A, Adv. Genet. 89: 179-233 (2015). Self-amplifying messenger RNA are also known as "self-replicating RNA" (also "SAM"). Examples of SAMs include alphavirus TC83-based vectors (see, Perri S, et al., J. Virol. 2003; 77:10394-10403) Flavivirus Based Vectors and West Nile virus-based vectors (see, Cu et al., Vaccines 367-383 (2013).

The term "messenger RNA" includes therapeutic mRNA that can be used to produce antibodies, e.g., prophylactic antibodies capable of protecting against infectious agents.

In a first embodiment the invention is a modified messenger RNA comprising an open reading frame that encodes a protein of interest, wherein said modified RNA comprises a modified nucleoside selected from the group consisting of:

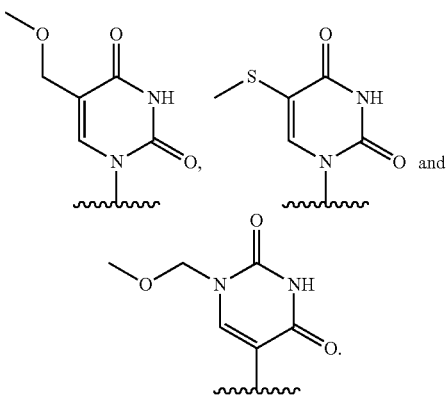

In a second embodiment, the invention is the modified messenger RNA according to the first embodiment, wherein said modified messenger RNA further comprises a 5'-terminal cap comprising $N^7$-methylguanine and a poly-A tail.

In a third embodiment, the invention the modified messenger RNA according to the second embodiment, wherein the cap of the modified messenger RNA comprises $m^7$GpppG cap or 3'-O-methyl-$m^7$GpppG cap.

In a fourth embodiment, the invention is the modified messenger RNA according to the first embodiment, wherein said RNA further comprises a cap-independent translational enhancer.

In a fifth embodiment, the invention is the modified messenger RNA according to the first embodiment, wherein said RNA further comprises 5' and/or 3' untranslated regions (UTRs) that enhance translation.

In a sixth embodiment, the invention is the modified messenger RNA according to the fifth embodiment, wherein said 5' and 3' UTRs comprise at least one UTR selected from the group consisting of a beta-globin 5' UTR, a tobacco etch virus (TEV) 5' UTR, and a beta-globin 3' UTR.

In a seventh embodiment, the invention is the modified messenger RNA according to the first embodiment, wherein said modified messenger RNA is present in a mammalian cell that is in culture, present in a tissue, or present in vivo in a mammal.

In an eighth embodiment, the invention is the modified messenger RNA according to the seventh embodiment, wherein the mammalian cell is a cell selected from the group consisting of an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stein cell, sustentacular cell, teloglial cell, and a zymogenic cell.

In a ninth embodiment, the invention is the modified messenger RNA according to the first embodiment, wherein said modified messenger RNA induces a detectably lower innate immune response than the same quantity of a corresponding unmodified messenger RNA.

In a tenth embodiment, the invention is the composition according to the ninth embodiment, wherein said detectably lower innate immune response is detected by a method selected from the group consisting of: (i) detecting that repeatedly contacting a mammalian cell with an amount of the modified messenger RNA that results in detectable expression of the encoded protein after a single contacting does not detectably reduce expression of the protein of interest, whereas repeatedly contacting the mammalian cell with the same quantity of said corresponding unmodified messenger RNA does detectably reduce expression of the encoded protein of interest; (ii) detecting that said modified messenger RNA results in a lower level of self-phosphorylation of RNA-activated protein kinase (PKR) and/or phosphorylation of eukaryotic translation initiation factor (eIF2α) compared to the same quantity of said corresponding unmodified messenger RNA based on an in vitro phosphorylation assay; (iii) detecting that the quantity of one or more cytokines induced by the mammalian cell in response to said corresponding unmodified messenger RNA is higher than the quantity of said one or more cytokines induced by the mammalian cell in response to said modified messenger RNA; (iv) detecting a difference in the level of expression of one or more dendritic cell (DC) activation markers in response to said corresponding unmodified messenger RNA compared to the level of expression of said one or more DC activation markers in response to the same quantity of said modified messenger RNA; (v) detecting a higher relative ability of said modified messenger RNA to act as an adjuvant for an adaptive immune response compared to the same quantity of said corresponding unmodified messenger RNA; (vi) detecting a higher level of activation of toll-like receptor (TLR) signaling molecules in response to said corresponding unmodified messenger RNA compared to the same quantity of said modified messenger RNA; and/or (vii) determining the quantity of said modified messenger RNA to elicit an immune response measured in any of cells (i)-(vi) compared to the quantity of said corresponding unmodified messenger to elicit the same immune response.

In an eleventh embodiment, the invention is the modified messenger RNA according to the tenth embodiment, wherein: said one or more cytokines in (iii) are selected from the group consisting of IL-12, IFN-α, TNF-α, RANTES, MIP-1α, MIP-1β, IL-6, IFN-β, and IL-8; said DC activation markers in (iv) are selected from the group consisting of: CD83, HLA-DR, CD80, and CD86; or said TLR signaling molecules in (vi) are selected from the group consisting of: TLR3, TLR7, and TLR8 signaling molecules.

In a twelfth embodiment, the invention is the modified messenger RNA according to the tenth embodiment, wherein said detectably lower innate immune response induced by said modified messenger RNA is at least 2-fold lower than the innate immune response induced by said corresponding unmodified messenger RNA using at least one of said cells for determining or measuring said detectable decrease in immunogenicity.

In a thirteenth embodiment, the invention is the modified messenger RNA according to the first embodiments, wherein said modified messenger RNA exhibits enhanced ability to produce said encoded protein of interest in said mammalian cell compared to the same quantity of an unmodified messenger RNA that exhibits the same sequence, wherein said enhanced ability to produce said protein of interest is determined by measuring a higher level of either the amount of protein or the amount of enzymatic activity or other biological effect produced at one or more times after contacting a mammalian cell with said modified messenger RNA compared to the corresponding amount of protein or amount of enzymatic activity or other biological effect produced in the same or equivalent mammalian cell at the same times after contacting with the same quantity of said corresponding unmodified messenger RNA.

In a fourteenth embodiment, the invention is the modified messenger RNA according to the thirteenth embodiment, wherein the ability to produce said encoded protein of interest in said mammalian cell is enhanced by at least 2-fold for said modified messenger RNA compared to said corresponding unmodified messenger RNA.

In a fifteenth embodiment, the invention is the modified messenger RNA according to the first embodiment, wherein said modified messenger RNA is encapsulated in a nanoparticle, polymer, lipid, cholesterol, or a cell penetrating peptide.

In a sixteenth embodiment, the invention is the modified messenger RNA according to the first embodiment, wherein said modified messenger RNA encodes a protein of interest selected from the group consisting of erythropoietin (EPO), a detectable enzyme selected from firefly luciferase, *Renilla* luciferase, bacterial beta-galactosidase (lacZ), green fluorescent protein (GFP), MYC, SRY, MCOP, platelet-derived growth factor (PDGF), vascular endothelial growth factor (VEGF), transforming growth factor-beta1 (TGF-beta1), insulin-like growth factor (IGF), alpha-melanocyte-stimulating hormone (alpha-MSH), insulin-like growth factor-I (IGF-I), IL-4, IL-13, IL-10, inducible nitric oxide synthase (iNOS), a heat shock protein, cystic fibrosis transmembrane conductance regulator (CFTR), an enzyme with antioxidant activity, catalase, phospholipid hydroperoxide glutathione peroxidase, superoxide dismutase-1, superoxide dismutase-2, Bruton's tyrosine kinase, adenosine deaminase, ectonucleoside triphosphate diphosphydrolase, ABCA4, ABCD3, ACADM, AGL, AGT, ALDH4A1, ALPL, AMPD1, APOA2, AVSD1, BRCD2, C1QA, C1QB, C1QG, C8A, C8B, CACNA1S, CCV, CD3Z, CDC2L1, CHML, CHS1, CIAS1, CLCNKB, CMD1A, CMH2, CMM, COL11A1, COL8A2, COL9A2, CPT2, CRB1, CSE, CSF3R, CTPA, CTSK, DBT, DIOL DISCI, DPYD, EKV, ENO1, ENO1P, EPB41, EPHX1, F13B, F5, FCGR2A, FCGR2B, FCGR3A, FCHL, FH, FMO3, FMO4, FUCA1, FY, GALE, GBA, GFND, GJA8, GJB3, GLC3B, HF1, HMGCL, HPC1, HRD, HRPT2, HSD3B2, HSPG2, KCNQ4, KCS, KIF1B, LAMB3, LAMC2, LGMD1B, LMNA, LOR, MCKD1, MCL1, MPZ, MTHFR, MTR, MUTYH, MYOC, NB, NCF2, NEM1, NPHS2, NPPA, NRAS, NTRK1, OPTA2, PBX1, PCHC, PGD, PHA2A, PHGDH, PKLR, PKP1, PLA2G2A, PLOD, PPDX, PPTO, PRCC, PRG4, PSEN2, PTOS1, REN, RFX5, RHD, RMD1, RPE65, SCCD, SERPINC1, SJS1, SLC19A2, SLC2A1, SPG23, SPTA1, TALL TNFSF6, TNNT2, TPM3, TSHB, UMPK, UOX, UROD, USH2A, VMGLOM, VWS, WS2B, ABCB11, ABCG5, ABCG8, ACADL, ACP1, AGXT, AHHR, ALMS1, ALPP, ALS2, APOB, BDE, BDMR, BJS, BMPR2, CHRNA1, CMCWTD, CNGA3, COL3A1, COLAA3, COL4A4, COL6A3, CPS1, CRYGA, CRYGEP1, CYP1B1, CYP27A1, DBI, DES, DYSF, EDAR, EFEMP1, EIF2AK3, ERCC3, FSHR, GINGF, GLC1B, GPD2, GYPC, HADHA, HADHB, HOXD13, HPE2, IGKC, IHH, IRS1, ITGA6, KHK, KYNU, LCT, LHCGR, LSFC, MSH2, MSH6, NEB, NMTC, NPHP1, PAFAH1P1, PAX3, PAX8, PMS1, PNKD, PPH1, PROC, REG1A, SAG, SFTPB, SLC11A1, SLC3A1, SOS1, SPG4, SRD5A2, TCL4, TGFA, TMD, TPO, UGT1A@, UV24, WSS, XDH, ZAP70, ZFHX1B, ACAA1, AGS1, AGTR1, AHSG, AMT, ARMET, BBS3, BCHE, BCPM, BTD, CASR, CCR2, CCR5, CDL1, CMT2B, COL7A1, CP, CPO, CRV, CTNNB1, DEM, ETM1, FANCD2, FIR, FOXL2, GBE1, GLB1, GLCLC, GNAI2, GNAT1, GP9, GPX1, HGD, HRG, ITIH1, KNG, LPP, LRS1, MCCC1, MDS1, MHS4, MITF, MLH1, MYL3, MYMY, OPA1, P2RY12, PBXP1, PCCB, POU1F1, PPARG, PROS1, PTHR1, RCA1, RHO, SCAT, SCLC1, SCN5A, SI, SLC25A20, SLC2A2, TF, TGFBR2, THPO, THRB, TKT, TM4SF1, TRH, UMPS, UQCRC1, USH3A, VHL, WS2A, XPC, ZNF35, ADH1B, ADH1C, AFP, AGA, AIH2, ALB, ASMD, BFHD, CNGA1, CRBM, DCK, DSPP, DTDP2, ELONG, ENAM, ETFDH, EVC, Flt, FABP2, FGA, FGB, FGFR3, FGG, FSHMDIA, GC, GNPTA, GNRHR, GYPA, HCA, HCL2, HD, HTN3, HVBS6, IDUA, IF, JPD, KIT, KLKB1, LQT4, MANBA, MLLT2, MSX1, MTP, NR3C2, PBT, PDE6B, PEE1, PITX2, PKD2, QDPR, SGCB, SLC25A4, SNCA, SOD3, STATH, TAPVR1, TYS, WBS2, WFS1, WHCR, ADAMTS2, ADRB2, AMCN, AP3B1, APC, ARSB, B4GALT7, BHR1, C6, C7, CCAL2, CKN1, CMDJ, CRHBP, CSF1R, DHFR, DIAPH1, DTR, EOS, EPD, ERVR, F12, FBN2, GDNF, GHR, GLRA1, GM2A, HEXB, HSD17B4, ITGA2, KFS, LGMDLA, LOX, LTC4S, MAN2A1, MCC, MCCC2, MSH3, MSX2, NR3C1, PCSK1, PDE6A, PFBI, RASA1, SCZD1, SDHA, SGCD, SLC22A5, SLC26A2, SLC6A3, SM1, SMA@, SMN1, SMN2, SPINK5, TCOF1, TELAB1, TGFBI, ALDH5A1, ARG1, AS, ASSP2, BCKDHB, BF, C2, C4A, CDKN1A, COL10A1, COL11A2, CYP21A2, DYX2, EJM1, ELOVL4, EPM2A, ESR1, EYA4, F13A1, FANCE, GCLC, GJA1, GLYS1, GMPR, GSE, HCR, HFE, HLA-A, HLA-DPB1, HLA-DRA, HPFH, ICS1, IDDM1, IFNGR1, IGAD1, IGF2R, ISCW, LAMA2, LAP, LCA5, LPA, MCDR1, MOCS1, MUT, MYB, NEU1, NKS1, NYS2, OA3, ODDD, OFC0, PARK2, PBCA, PBCRA1, PDB1, PEX3, PEX6, PEX7, PKHD1, PLA2G7, PLG, POLH, PPAC, PSORS1, PUJO, RCD1, RDS, RHAG, RP14, RUNX2, RWS, SCA1, SCZD3, SIASD, SOD2, ST8, TAP1, TAP2, TFAP2B, TNDM, TNF, TPBG, TPMT, TULP1, WISP3, AASS, ABCB1, ABCB4, ACHE, AQP1, ASL, ASNS, AUTS1, BPGM, BRAF, C7orf2, CACNA2D1, CCM1, CD36, CFTR, CHORDOMA, CLCN1, CMH6, CMT2D, COL1A2, CRS, CYMD, DFNA5, DLD, DYT11, EEC1, ELN, ETV1, FKBP6, GCK, GHRHR, GHS, GLI3, GPDS1, GUSB, HLXB9, HOXA13, HPFH2, HRX, IAB, IMMP2L, KCNH2, LAMB1, LEP, MET, NCF1, NM, OGDH, OPN1SW, PEX1, PGAM2, PMS2, PON1, PPP1R3A, PRSS1, PTC, PTPN12, RP10, RP9, SERPINE1, SGCE, SHFM1, SHH, SLC26A3, SLC26A4, SLOS, SMAD1, TBXAS1, TWIST, ZWS1, ACHM3, ADRB3, ANK1, CA1, CA2, CCAL1, CLN8, CMT4A, CNGB3, COH1, CPP, CRH, CYP11B1, CYP11B2, DECR1, DPYS, DURS1, EBS1, ECA1, EGI, EXT1, EYA1, FGFR1, GNRH1, GSR, GULOP, HR, KCNQ3, KFM, KWE, LGCR, LPL, MCPH1, MOS, MYC, NAT1, NAT2, NBS1, PLAT, PLEC1, PRKDC, PXMP3, RP1, SCZD6, SFTPC, SGM1, SPG5A, STAR, TG, TRPS1, TTPA, VMD1, WRN, ABCA1, ABL1, ABO, ADAMTS13, AK1, ALAD, ALDH1A1, ALDOB, AMBP, AMCD1, ASS, BDMF, BSCL, C5, CDKN2A, CHAC, CLA1, CMD1B, COL5A1, CRAT, DBH, DNAI1, DYS, DYT1, ENG, FANCC, FBP1, FCMD, FRDA, GALT, GLDC, GNE, GSM1, GSN, HSD17B3, HSN1, IBM2, INVS, JBTS1, LALL, LCCS1, LCCS, LGMD2H, LMX1B, MLLT3, MROS, MSSE, NOTCH1, ORM1, PAPPA, PIP5K1B, PTCH, PTGS1, RLN1, RLN2, RMRP, ROR2, RPD1, SARDH, SPTLC1, STOM, TDFA, TEK, TMC1, TRIM32, TSC1, TYRP1, XPA, CACNB2, COL17A1, CUBN, CXCL12, CYP17, CYP2C19, CYP2C9, EGR2, EMX2, ERCC6, FGFR2, HK1, HPS1, IL2RA, LGI1, LIPA, MAT1A, MBL2, MKI67, MXI1, NODAL, OAT, OATL3, PAX2, PCBD, PEO1, PHYH, PNLIP, PSAP, PTEN, RBP4, RDPA, RET, SFTPA1, SFTPD, SHFM3, SIAL, THC2, TLX1, TNFRSF6, UFS, UROS, AA, ABCC8, ACAT1, ALX4, AMPD3, ANC, APOAL, APOA4, APOC3, ATM, BSCL2, BWS, CALCA, CAT, CCND1, CD3E, CD3G, CD59, CDKNLC, CLN2, CNTF, CPT1A, CTSC, DDB1, DDB2, DHCR7, DLAT, DRD4, ECB2, ED4, EVR1, EXT2, F2, FSHB, FTH1, G6PT1, G6PT2, GIF, HBB, HBBP1, HBD, HBE1, HBG1, HBG2, HMBS, HND, HOMG2, HRAS, HVBS1, IDDM2, IGER, INS, JBS, KCNJ11, KCNJ1, KCNQ1, LDHA, LRP5, MEN1, MLL, MYBPC3, MYO7A, NNO1, OPPG, OPTB1, PAX6, PC, PDX1, PGL2, PGR, PORC, PTH, PTS, PVRL1, PYGM, RAG1, RAG2, ROM1, RRAS2, SAA1, SCA5, SCZD2, SDHD, SERPING1, SMPD1, TCIRG1, TCL2, TECTA, TH, TREH, TSG101, TYR, USHIC, VMD2, VRNI, WT1, WT2, ZNF145, A2M, AAAS, ACADS, ACLS, ACVRL1, ALDH2, AMHR2, AOM, AQP2, ATD, ATP2A2, BDC, CIR, CD4, CDK4, CNA1, COL2A1, CYP27B1, DRPLA, ENUR2, FEOM1, FGF23, FPF, GNB3, GNS, HAL, HBP1, HMGA2, HMN2, HPD, IGF1, KCNA1, KERA, KRAS2, KRT1, KRT2A, KRT3, KRT4, KRT5, KRT6A, KRT6B, KRTHB6, LDHB, LYZ, MGCT, MPE, MVK, MYL2, OAP, PAH, PPKB, PRB3, PTPN11, PXR1, RLS, RSN, SAS, SAX1, SCA2, SCNN1A, SMAL, SPPM, SPSMA, TBX3, TBX5, TCF1, TPI1, TSC3, ULR, VDR, VWF, ATP7B, BRCA2, BRCD1, CLN5, CPB2, ED2, EDNRB, ENUR1, ERCC5, F10, F7, GJB2, GJB6, IPF1, MBS1, MCOR, NYS4, PCCA, RB1, RHOK, SCZD7, SGCG, SLC10A2, SLC25A15, STARP1, ZNF198, ACHM1, ARVD1, BCH, CTAA1, DAD1, DFNB5, EML1, GALC, GCH1, IBGC1, IGH@, IGHC group, IGHG1, IGHM, IGHR, IV, LTBP2, MJD, MNG1, MPD1, MPS3C, MYH6, MYH7, NP, NPC2, PABPN1, PSEN1, PYGL, RPGRIP1, SERPINA1, SERPINA3, SERPINA6, SLC7A7, SPG3A, SPTB, TCL1A, TGM1, TITF1, TMIP, TRA@, TSHR, USHLA, VP, ACCPN, AHO2, ANCR, B2M, BBS4, BLM, CAPN3, CDAN1, CDAN3, CLN6, CMH3, CYP19, CYP1A1, CYP1A2, DYX1, EPB42, ETFA, EYCL3, FAH, FBN1, FES, HCVS, HEXA, IVD, LCS1, LIPC, MY05A, OCA2, OTSC1, PWCR, RLBP1, SLC12A1, SPG6, TPM1, UBE3A, WMS, ABCC6, ALDOA, APRT, ATP2A1, BBS2, CARD15, CATM, CDH1, CETP, CHST6, CLN3, CREBBP, CTH, CTM, CYBA, CYLD, DHS, DNASE1, DPEP1, ERCC4, FANCA, GALNS, GAN, HAGH, HBA1, HBA2, HBHR, HBQ1, HBZ, HBZP, HP, HSD11B2, IL4R, LIPB, MC1R, MEFV, MHC2TA, MLYCD, MMVP1, PHKB, PHKG2, PKD1, PKDTS, PMM2, PXE, SALL1, SCA4, SCNN1B, SCNN1G, SLC12A3, TAT, TSC2, VD1, WT3, ABR, ACACA, ACADVL, ACE, ALDH3A2, APOH, ASPA, AXIN2, BCL5, BHD, BLMH, BRCA1, CACD, CCA1, CCZS, CHRNB1, CHRNE, CMT1A, COL1A1, CORDS, CTNS, EPX, ERBB2, G6PC, GAA, GALK1, GCGR, GFAP, GH1, GH2, GP1BA, GPSC, GUCY2D, ITGA2B, ITGB3, ITGB4, KRT10, KRT12, KRT13, KRT14, KRT14L1, KRT14L2, KRT14L3, KRT16, KRT16L1, KRT16L2, KRT17, KRT9, MAPT, MDB, MDCR, MGI, MHS2, MKS1, MPO, MYO15A, NAGLU, NAPB, NF1, NME1, P4HB, PAFAH1B1, PECAM1, PEX12, PHB, PMP22, PRKAR1A, PRKCA, PRKWNK4, PRP8, PRPF8, PTLAH, RARA, RCV1, RMSA1, RP17, RSS, SCN4A, SERPINF2, SGCA, SGSH, SHBG, SLC2A4, SLC4A1, SLC6A4, SMCR, SOST, SOX9, SSTR2, SYM1, SYNS1, TCF2, THRA, TIMP2, TOC, TOP2A, TP53, TRIM37, VBCH, ATP8B1, BCL2, CNSN, CORD1, CYB5, DCC, F5F8D, FECH, FEO, LAMA3, LCFS2, MADH4, MAFD1, MC2R, MCL, MYP2, NPC1, SPPK, TGFBRE, TGIF, TTR, AD2, AMH, APOC2, APOE, ATHS, BAX, BCKDHA, BCL3, BFIC, C3, CACNA1A, CCO, CEACAM5, COMP, CRX, DBA, DDU, DFNA4, DLL3, DM1, DMWD, E11S, ELA2, EPOR, ERCC2, ETFB, EXT3, EYCL1, FTL, FUT1, FUT2, FUT6, GAMT, GCDH, GPI, GUSM, HB1, HCL1, HHC2, HHC3, ICAM3, INSR, JAK3, KLK3, LDLR, LHB, LIG1, LOH19CR1, LYL1, MAN2B1, MCOLN1, MDRV, MLLT1, NOTCH3, NPHS1, OFC3, OPA3, PEPD, PRPF31, PRTN3, PRX, PSG1, PVR, RYR1, SLC5A5, SLC7A9, STK11, TBXA2R, TGFB1, TNNI3, TYROBP, ADA, AHCY, AVP, CDAN2, CDPD1, CHED1, CHED2, CHRNA4, CST3, EDN3, EEGV1, FTLL1, GDF5, GNAS, GSS, HNF4A, JAG1, KCNQ2, MKKS, NBIA1, PCK1, PI3, PPCD, PPGB, PRNP, THBD, TOP1, AIRE, APP, CBS, COL6A1, COL6A2, CSTB, DCR, DSCR1, FPDMM, HLCS, HPE1, ITGB2, KCNE1, KNO, PRSS7, RUNX1, SOD1, TAM, ADSL, ARSA, BCR, CECR, CHEK2, COMT, CRYBB2, CSF2RB, CTHM, CYP2D6, CYP2D7P1, DGCR, DIA1, EWSR1, GGT1, MGCR, MN1, NAGA, NE2, OGS2, PDGFB, PPARA, PRODH, SCO2, SCZD4, SERPIND1, SLC5A1, SOX10, TCN2, TIMP3, TST, VCF, ABCD1, ACTL1, ADFN, AGMX2, AHDS, AIC, AIED, AIH3, ALAS2, AMCD, AMELX, ANOP1, AR, ARAF1, ARSC2, ARSE, ARTS, ARX, ASAT, ASSP5, ATP7A, ATRX, AVPR2, BFLS, BGN, BTK, BZX, C1HR, CACNA1F, CALB3, CBBM, CCT, CDR1, CFNS, CGF1, CHM, CHR39c, CIDX, CLA2, CLCN5, CLS, CMTX2, CMTX3, CND, COD1, COD2, COL4A5, COL4A6, CPX, CVD1, CYBB, DCX, DFN2, DFN4, DFN6, DHOF, DIAPH2, DKC1, DMD, DSS, DYT3, EBM, EBP, ED1, ELK1, EMD, EVR2, F8, F9, FCP1, FDPSL5, FGD1, FGS1, FMR1, FMR2, G6PD, GABRA3, GATA1, GDI1, GDXY, GJB1, GK, GLA, GPC3, GRPR, GTD, GUST, HMS1, HPRT1, HPT, HTC2, HTR2c, HYR, IDS, IHG1, IL2RG, INDX, IP1, IP2, JMS, KAL1, KFSD, L1CAM, LAMP2, MAA, MAFD2, MAOA, MAOB, MCF2, MCS, MEAX, MECP2, MF4, MGC1, MIC5, MID1, MLLT7, MLS, MRSD, MRX14, MRX1, MRX20, MRX2, MRX3, MRX40, MRXA, MSD, MTM1, MYCL2, MYP1, NDP, NHS, NPHL1, NROB1, NSX, NYS1, NYX, OA1 OASD, OCRL, ODT1, OFD1, OPA2, OPD1, OPEM, OPN1LW, OPN1MW, OTC, P3, PDHA1, PDR, PFC, PFKFB1, PGK1, PGK1P1, PGS, PHEX, PHKA1, PHKA2, PHP, PIGA, PLP1, POF1, POLA, POU3F4, PPMX, PRD, PRPS1, PRPS2, PRS, RCCP2, RENBP, RENS1, RP2, RP6, RPGR, RPS4X, RPS6KA3, RS1, S11, SDYS, SEDL, SERPINA7, SH2D1A, SHFM2, SLC25A5, SMAX2, SRPX, SRS, STS, SYN1, SYP, TAF1, TAZ, TBX22, TDD, TFE3, THAS, THC, TIMM8A, TIM1, TKCR, TNFSF5, UBE1, UBE2A, WAS, WSN, WTS, WWS, XIC, XIST, XK, XM, XS, ZFX, ZIC3, ZNF261, ZNF41, ZNF6, AMELY, ASSP6, AZF1, AZF2, DAZ, GCY, RPS4Y, SMCY, ZFY, ABAT, AEZ, AFA, AFD1, ASAH1, ASD1, ASMT, CCAT, CECR9, CEPA, CLA3, CLN4, CSF2RA, CTS1, DF, DIH1, DWS, DYT2, DYT4, EBR3, ECT, EEF1A1L14, EYCL2, FANCB, GCSH, GCSL, GIP, GTS, HHG, HMI, HOAC, HOKPP2, HRPT1, HSD3B3, HTC1, HV1S, ICHQ, ICR1, ICR5, IL3RA, KAL2, KMS, KRT18, KSS, LCAT, LHON, LIMM, MANBB, MCPH2, MEB, MELAS, MIC2, MPFD, MS, MSS, MTATP6, MTCO1, MTCO3, MTCYB, MTND1, MTND2, MTND4, MTND5, MTND6, MTRNR1, MTRNR2, MTTE, MTTG, MTTI, MTTK, MTTL1, MTTL2, MTTN, MTTP, MTTS1, NAMSD, OCD1, OPD2, PCK2, PCLD, PCOS1, PFKM, PKD3, PRCA1, PRO1, PROP1, RBS, RFXAP, RP, SHOX, SLC25A6, SPG5B, STO, SUOX, THM, TTD and antibodies. In more specific embodiments, the antibody is selected from the group consisting of anti-interleukin-1 β antibody (see, canakinumab; Ilaris®; EP1313769B2 (Novartis AG); U.S. Pat. No. 7,446, 175 (Gram et al.) and U.S. Pat. No. 8,409,576 (Lowe et al.); CHEMBL1201834; Dhimolea, "Canakinumab". MAbs 2 (1): 3-13 (2010)) and anti-YFV antibody (e.g., 2D12, Schlesinger et al. "Monoclonal antibodies distinguish between wild and vaccine strains of yellow fever virus by neutralization, hemagglutination inhibition, and immune precipitation of the virus envelope protein." Virology 125: 8-17 (1983)).

In a seventeenth embodiment, the invention is the modified messenger RNA according to the first embodiment, wherein said modified messenger RNA is synthesized by in vitro transcription in a reaction mixture comprising a 5'-triphosphate derivative of a modified nucleoside selected from the group consisting of:

In an eighteenth embodiment, the invention is the modified messenger RNA according to the first embodiment, wherein said modified messenger RNA further comprises a modified nucleoside selected from the group consisting of 5-methylcytidine ($m^5C$), pseudouridine ($\Psi$), 1-methypseudouridine ($m^1\Psi$), 5-methyluridine ($m^5U$), $N^6$-methyladenosine ($m^6A$), 2-thiouridine ($S^2U$) and 2'-O-methyluridine (2'-O-methyl-U), In a nineteenth embodiment, the invention is the modified messenger RNA according to the eighteenth embodiment, wherein said modified messenger RNA exhibits a detectable decrease in immunogenicity to said mammalian cell compared to the same quantity of said corresponding unmodified messenger RNA.

In a twentieth embodiment, the invention is the modified messenger RNA according to the eighteenth embodiment, wherein said modified messenger RNA is synthesized by in vitro transcription in a reaction mixture comprising a 5'-triphosphate derivatives selected from the group consisting of

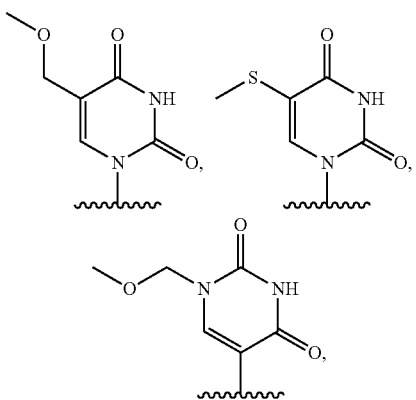

and a 5'-triphosphate derivatives selected from the group consisting of 5-methylcytidine (m⁵C), pseudouridine (Ψ), 1-methypseudouridine (m¹Ψ), 5-methyluridine (m⁵U), $N^6$-methyladenosine (m⁶A), 2-thiouridine ($S^2U$) and 2'-O-methyluridine (2'-O-methyl-U).

In a twenty-first embodiment, the invention is the modified messenger RNA according to the eighteenth embodiment, wherein said modified messenger RNA is present in a mammalian cell that is in culture, present in a tissue, or present in vivo in a mammal.

In one embodiment, the invention is the modified messenger RNA according to any of the preceding embodiments, wherein the messenger RNA comprises the nucleoside:

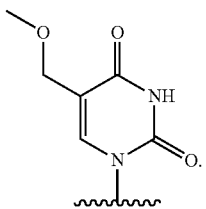 [SMILES: *n1cc(COC)c(=O)[nH]c1=O]

In another embodiment, the invention is the modified messenger RNA according to any of the preceding embodiments, wherein the messenger RNA comprises the nucleoside:

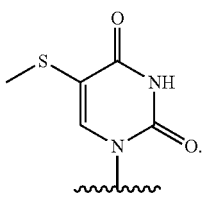 [SMILES: *n1cc(SC)c(=O)[nH]c1=O]

In yet another embodiment, the invention is the modified messenger RNA according to any of the preceding embodiments, wherein the messenger RNA comprises the nucleoside:

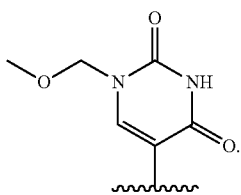

In a twenty-second embodiment, the invention is a method for inducing a mammalian cell to produce a protein of interest comprising the step of: repeatedly administering to said mammalian cell modified messenger RNA comprising an open reading frame that encodes a protein of interest, wherein said modified messenger RNA comprises at least one modified nucleoside selected from the group consisting of

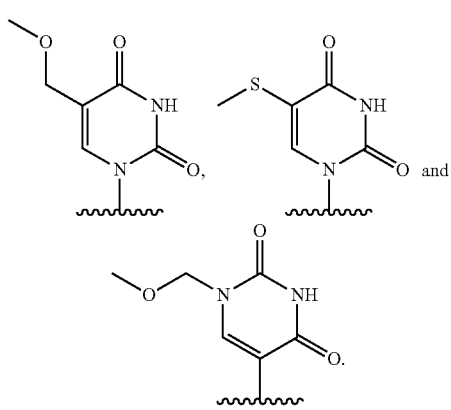

In a twenty-third embodiment, the invention is the method according to the twenty-second embodiment, wherein said modified messenger RNA further comprises a poly-A tail.

In a twenty-fourth embodiment, the invention is the method according to the twenty-second embodiment, wherein said modified messenger RNA further comprises a m⁷GpppG cap or a 3'-O-methyl-m⁷GpppG cap.

In a twenty-fifth embodiment, the invention is the method according to the twenty-second embodiment, wherein said modified messenger RNA further comprises a cap-independent translational enhancer.

In a twenty-sixth embodiment, the invention is the method according to the twenty-second embodiment, wherein said modified messenger RNA further comprises 5' and/or 3' untranslated regions that enhance translation.

In a twenty-seventh embodiment, the invention is the method according to the twenty-second embodiment, wherein said modified messenger RNA induces a detectably lower innate immune response than the same quantity of an unmodified messenger RNA that exhibits the same sequence.

In a twenty-eighth embodiment, the invention is the method according to the twenty-seventh embodiment, wherein said detectably lower innate immune response is detected by at least one method selected from the group consisting of: (i) detecting that repeatedly contacting a mammalian cell with an amount of the modified messenger RNA that results in detectable expression of the encoded protein after a single contacting does not detectably reduce expression of the protein of interest, whereas repeatedly contacting the mammalian cell with the same quantity of the unmodified messenger RNA that exhibits the same sequence does detectably reduce expression of the encoded protein of interest; (ii) detecting that said modified messenger RNA results in a lower level of self-phosphorylation of RNA-activated protein kinase (PKR) or phosphorylation of the eukaryotic translation initiation factor (eIF2α) compared to the same quantity of said corresponding unmodified messenger RNA based on an in vitro phosphorylation assay; (iii) detecting that the quantity of at least one cytokine induced by the mammalian cell in response to said corresponding unmodified messenger RNA that exhibits the same sequence is higher than the quantity of said at least one cytokine induced by the mammalian cell in response to said modified messenger RNA; (iv) detecting a difference in the level of expression of at least one dendritic cell (DC) activation marker in response to said corresponding unmodified messenger RNA compared to the level of expression of said at least one DC activation marker in response to the same quantity of said modified messenger RNA; (v) detecting a higher relative ability of said modified messenger RNA to act as an adjuvant for an adaptive immune response compared to the same quantity of said corresponding unmodified messenger RNA; (vi) detecting a higher level of activation of toll-like receptor (TLR) signaling molecules in response to unmodified messenger RNA that exhibits the same sequence compared to the same quantity of said modified messenger RNA; and/or (vii) determining the quantity of said modified messenger RNA that elicits an immune response measured in any of methods (i)-(vi) compared to the quantity of unmodified messenger RNA to elicit the same immune response.

In a twenty-ninth embodiment, the invention is the method according to the twenty-eighth embodiment, wherein: said at least one cytokine in (iii) is selected from the group consisting of: IL-12, IFN-α, TNF-α, RANTES, MIP-1α, MIP-1β, IL-6, IFN-β, and IL-8; said DC activation marker in (iv) is selected from the group consisting of: CD83, HLA-DR; CD80, and CD86; or said TLR signaling molecule in (vi) is selected from the group consisting of: TLR3, TLR7, and TLR8 signaling molecules.

In a thirtieth embodiment, the invention is the method according to the twenty-eighth embodiment, wherein said detectably lower innate immune response induced by said modified messenger RNA is at least 2-fold lower than the innate immune response induced by said unmodified messenger RNA using at least one of said methods for determining or measuring said detectable decrease in immunogenicity.

In a thirty-first embodiment, the invention is the method according to the twenty-second embodiment, wherein said modified messenger RNA exhibits enhanced ability to produce said encoded protein of interest in said mammalian cell compared to the same quantity of said corresponding unmodified messenger RNA that, wherein said enhanced ability to produce said protein of interest is determined by measuring a higher level of either the amount of protein or the amount of enzymatic activity or other biological effect produced at one or more times after said contacting of said mammalian cell with said modified messenger RNA than the corresponding amount of protein or amount of enzymatic activity or other biological effect produced in the same or equivalent mammalian cell at the same times after contacting with the same quantity of said corresponding unmodified messenger RNA.

In a thirty-second embodiment, the invention is the method according to the thirty-first embodiment, wherein the ability to produce said encoded protein of interest in said mammalian cell is enhanced by at least 2-fold for said modified messenger RNA compared with said unmodified messenger RNA.

In a thirty-third embodiment, the invention is the method according to the twenty-second embodiment, wherein said modified messenger RNA is subsequently encapsulated in a nanoparticle, lipid, polymer, cholesterol, or cell penetrating peptide.

In a thirty-fourth embodiment, the invention is the method of the twenty-second embodiment, wherein said protein of interest is a protein selected from the group consisting of erythropoietin (EPO), a detectable enzyme selected from firefly luciferase, Renilla luciferase, bacterial beta-galactosidase (lacZ), green fluorescent protein (GFP), MYC, SRY, MCOP, platelet-derived growth factor (PDGF), vascular endothelial growth factor (VEGF), transforming growth factor-beta1 (TGF-beta1), insulin-like growth factor (IGF), alpha-melanocyte-stimulating hormone (alpha-MSH), insulin-like growth factor-I (IGF-I), IL-4, IL-13, IL-10, inducible nitric oxide synthase (iNOS), a heat shock protein, cystic fibrosis transmembrane conductance regulator (CFTR), an enzyme with antioxidant activity, catalase, phospholipid hydroperoxide glutathione peroxidase, superoxide dismutase-1, superoxide dismutase-2, Bruton's tyrosine kinase, adenosine deaminase, ecto-nucleoside triphosphate diphosphydrolase, ABCA4, ABCD3, ACADM, AGL, AGT, ALDH4A1, ALPL, AMPD1, APOA2, AVSD1, BRCD2, C1QA, C1QB, C1QG, C8A, C8B, CACNA1S, CCV, CD3Z, CDC2L1, CHML, CHS1, CIAS1, CLCNKB, CMD1A, CMH2, CMM, COL11A1, COL8A2, COL9A2, CPT2, CRB1, CSE, CSF3R, CTPA, CTSK, DBT, DIO1, DISC1, DPYD, EKV, ENO1, ENO1P, EPB41, EPHX1, F13B, F5, FCGR2A, FCGR2B, FCGR3A, FCHL, FH, FMO3, FMO4, FUCA1, FY, GALE, GBA, GFND, GJA8, GJB3, GLC3B, HF1, HMGCL, HPC1, HRD, HRPT2, HSD3B2, HSPG2, KCNQ4, KCS, KIF1B, LAMB3, LAMC2, LGMD1B, LMNA, LOR, MCKD1, MCL1, MPZ, MTHFR, MTR, MUTYH, MYOC, NB, NCF2, NEM1, NPHS2, NPPA, NRAS, NTRK1, OPTA2, PBX1, PCHC, PGD, PHA2A, PHGDH, PKLR, PKP1, PLA2G2A, PLOD, PPDX, PPTO, PRCC, PRG4, PSEN2, PTOS1, REN, RFX5, RHD, RMD1, RPE65, SCCD, SERPINC1, SJS1, SLC19A2, SLC2A1, SPG23, SPTA1, TAL1, TNFSF6, TNNT2, TPM3, TSHB, UMPK, UOX, UROD, USH2A, VMGLOM, VWS, WS2B, ABCB11, ABCG5, ABCG8, ACADL, ACP1, AGXT, AHHR, ALMS1, ALPP, ALS2, APOB, BDE, BDMR, BJS, BMPR2, CHRNA1, CMCWTD, CNGA3, COL3A1, COLAA3, COL4A4, COL6A3, CPS1, CRYGA, CRYGEP1, CYP1B1, CYP27A1, DBI, DES, DYSF, EDAR, EFEMP1, EIF2AK3, ERCC3, FSHR, GINGF, GLC1B, GPD2, GYPC, HADHA, HADHB, HOXD13, HPE2, IGKC, IHH, IRS1, ITGA6, KHK, KYNU, LCT, LHCGR, LSFC, MSH2, MSH6, NEB, NMTC, NPHP1, PAFAH1P1, PAX3, PAX8, PMS1, PNKD, PPH1, PROC, REG1A, SAG, SFTPB, SLC11A1, SLC3A1, SOS1, SPG4, SRD5A2, TCL4, TGFA, TMD, TPO, UGT1A@, UV24, WSS, XDH, ZAP70, ZFHX1B, ACAA1, AGS1, AGTR1, AHSG, AMT, ARMET, BBS3, BCHE, BCPM, BTD, CASR, CCR2, CCR5, CDL1, CMT2B, COL7A1, CP, CPO, CRV, CTNNB1, DEM, ETM1, FANCD2, FIH, FOXL2, GBE1, GLB1, GLCLC, GNAI2, GNAT1, GP9, GPX1, HGD, HRG, ITIH1, KNG, LPP, LRS1, MCCC1, MDS1, MHS4, MITF, MLH1, MYL3, MYMY, OPA1, P2RY12, PBXP1, PCCB, POU1F1, PPARG, PROS1, PTHR1, RCA1, RHO, SCA7, SCLC1, SCN5A, SI, SLC25A20, SLC2A2, TF, TGFBR2, THPO, THRB, TKT, TM4SF1, TRH, UMPS, UQCRC1, USH3A, VHL, WS2A, XPC, ZNF35, ADH1B, ADH1C, AFP, AGA, AIH2, ALB, ASMD, BFHD, CNGA1, CRBM, DCK, DSPP, DTDP2, ELONG, ENAM, ETFDH, EVC, F11, FABP2, FGA, FGB, FGFR3, FGG, FSHMDIA, GC, GNPTA, GNRHR, GYPA, HCA, HCL2, HD, HTN3, HVBS6, IDUA, IF, JPD, KIT, KLKB1, LQT4, MANBA, MLLT2, MSX1, MTP, NR3C2, PBT, PDE6B, PEE1, PITX2, PKD2, QDPR, SGCB, SLC25A4, SNCA, SOD3, STATH, TAPVR1, TYS, WBS2, WFS1, WHCR, ADAMTS2, ADRB2, AMCN, AP3B1, APC, ARSB, B4GALT7, BHR1, C6, C7, CCAL2, CKN1, CMDJ, CRHBP, CSF1R, DHFR, DIAPH1, DTR, EOS, EPD, ERVR, F12, FBN2, GDNF, GHR, GLRA1, GM2A, HEXB, HSD17B4, ITGA2, KFS, LGMDLA, LOX, LTC4S, MAN2A1, MCC, MCCC2, MSH3, MSX2, NR3C1, PCSK1, PDE6A, PFBI, RASA1, SCZD1, SDHA, SGCD, SLC22A5, SLC26A2, SLC6A3, SM1, SMA@, SMN1, SMN2, SPINK5, TCOF1, TELAB1, TGFBI, ALDH5A1, ARG1, AS, ASSP2, BCKDHB, BF, C2, C4A, CDKN1A, COL10A1, COL11A2, CYP21A2, DYX2, EJM1, ELOVL4, EPM2A, ESR1, EYA4, F13A1, FANCE, GCLC, GJA1, GLYS1, GMPR, GSE, HCR, HFE, HLA-A, HLA-DPB1, HLA-DRA, HPFH, ICS1, IDDM1, IFNGR1, IGAD1, IGF2R, ISCW, LAMA2, LAP, LCA5, LPA, MCDR1, MOCS1, MUT, MYB, NEU1, NKS1, NYS2, OA3, ODDD, OFC0, PARK2, PBCA, PBCRA1, PDB1, PEX3, PEX6, PEX7, PKHD1, PLA2G7, PLG, POLH, PPAC, PSORS1, PUJO, RCD1, RDS, RHAG, RP14, RUNX2, RWS, SCA1, SCZD3, SIASD, SOD2, ST8, TAP1, TAP2, TFAP2B, TNDM, TNF, TPBG, TPMT, TULP1, WISP3, AASS, ABCB1, ABCB4, ACHE, AQP1, ASL, ASNS, AUTS1, BPGM, BRAF, C7orf2, CACNA2D1, CCM1, CD36, CFTR, CHORDOMA, CLCN1, CMH6, CMT2D, COL1A2, CRS, CYMD, DFNA5, DLD, DYT11, EEC1, ELN, ETV1, FKBP6, GCK, GHRHR, GHS, GLI3, GPDS1, GUSB, HLXB9, HOXA13, HPFH2, HRX, IAB, IMMP2L, KCNH2, LAMBI, LEP, MET, NCF1, NM, OGDH, OPN1SW, PEX1, PGAM2, PMS2, PON1, PPP1R3A, PRSS1, PTC, PTPN12, RP10, RP9, SERPINE1, SGCE, SHFM1, SHH, SLC26A3, SLC26A4, SLOS, SMAD1, TBXAS1, TWIST, ZWS1, ACHM3, ADRB3, ANK1, CA1, CA2, CCAL1, CLN8, CMT4A, CNGB3, COH1, CPP, CRH, CYP11B1, CYP11B2, DECR1, DPYS, DURS1, EBS1, ECA1, EGI, EXT1, EYA1, FGFR1, GNRH1, GSR, GULOP, HR, KCNQ3, KFM, KWE, LGCR, LPL, MCPH1, MOS, MYC, NAT1, NAT2, NBS1, PLAT, PLEC1, PRKDC, PXMP3, RP1, SCZD6, SFTPC, SGM1, SPG5A, STAR, TG, TRPS1, TTPA, VMD1, WRN, ABCA1, ABL1, ABO, ADAMTS13, AK1, ALAD, ALDH1A1, ALDOB, AMBP, AMCD1, ASS, BDMF, BSCL, C5, CDKN2A, CHAC, CLA1, CMD1B, COL5A1, CRAT, DBH, DNAI1, DYS, DYT1, ENG, FANCC, FBP1, FCMD, FRDA, GALT, GLDC, GNE, GSM1, GSN, HSD17B3, HSN1, IBM2, INVS, JBTS1, LALL, LCCS1, LCCS, LGMD2H, LMX1B, MLLT3, MROS, MSSE, NOTCH1, ORM1, PAPPA, PIP5K1B, PTCH, PTGS1, RLN1, RLN2, RMRP, ROR2, RPD1, SARDH, SPTLC1, STOM, TDFA, TEK, TMC1, TRIM32, TSC1, TYRP1, XPA, CACNB2, COL17A1, CUBN, CXCL12, CYP17, CYP2C19, CYP2C9, EGR2, EMX2, ERCC6, FGFR2, HK1, HPS1, IL2RA, LGI1, LIPA, MAT1A, MBL2, MKI67, MXI1 NODAL, OAT, OATL3, PAX2, PCBD, PEO1, PHYH, PNLIP, PSAP, PTEN, RBP4, RDPA, RET, SFTPA1, SFTPD, SHFM3, SIAL, THC2, TLX1, TNFRSF6, UFS, UROS, AA, ABCC8, ACAT1, ALX4, AMPD3, ANC, APOAL, APOA4, APOC3, ATM, BSCL2, BWS, CALCA, CAT, CCND1, CD3E, CD3G, CD59, CDKNLC, CLN2, CNTF, CPT1A, CTSC, DDB1, DDB2, DHCR7, DLAT, DRD4, ECB2, ED4, EVR1, EXT2, F2, FSHB, FTH1, G6PT1, G6PT2, GIF, HBB, HBBP1, HBD, HBE1, HBG1, HBG2, HMBS, HND, HOMG2, HRAS, HVBS1, IDDM2, IGER, INS, JBS, KCNJ11, KCNJ1, KCNQ1, LDHA, LRP5, MEN1, MLL, MYBPC3, MYO7A, NNO1, OPPG, OPTB1, PAX6, PC, PDX1, PGL2, PGR, PORC, PTH, PTS, PVRL1, PYGM, RAG1, RAG2, ROM1, RRAS2, SAA1, SCA5, SCZD2, SDHD, SERPING1, SMPD1, TCIRG1, TCL2, TECTA, TH, TREH, TSG101, TYR, USHIC, VMD2, VRNI, WT1, WT2, ZNF145, A2M, AAAS, ACADS, ACLS, ACVRL1, ALDH2, AMHR2, AOM, AQP2, ATD, ATP2A2, BDC, CIR, CD4, CDK4, CNA1, COL2A1, CYP27B1, DRPLA, ENUR2, FEOM1, FGF23, FPF, GNB3, GNS, HAL, HBP1, HMGA2, HMN2, HPD, IGF1, KCNA1, KERA, KRAS2, KRT1, KRT2A, KRT3, KRT4, KRT5, KRT6A, KRT6B, KRTHB6, LDHB, LYZ, MGCT, MPE, MVK, MYL2, OAP, PAH, PPKB, PRB3, PTPN11, PXR1, RLS, RSN, SAS, SAX1, SCA2, SCNN1A, SMAL, SPPM, SPSMA, TBX3, TBX5, TCF1, TPI1, TSC3, ULR, VDR, VWF, ATP7B, BRCA2, BRCD1, CLN5, CPB2, ED2, EDNRB, ENUR1, ERCC5, F10, F7, GJB2, GJB6, IPF1, MBS1, MCOR, NYS4, PCCA, RB1, RHOK, SCZD7, SGCG, SLC10A2, SLC25A15, STARP1, ZNF198, ACHM1, ARVD1, BCH, CTAA1, DAD1, DFNB5, EML1, GALC, GCH1, IBGC1, IGH@, IGHC group, IGHG1, IGHM, IGHR, IV, LTBP2, MJD, MNG1, MPD1, MPS3C, MYH6, MYH7, NP, NPC2, PABPN1, PSEN1, PYGL, RPGRIP1, SERPINA1, SERPINA3, SERPINA6, SLC7A7, SPG3A, SPTB, TCL1A, TGM1, TITF1, TMIP, TRA@, TSHR, USHLA, VP, ACCPN, AHO2, ANCR, B2M, BBS4, BLM, CAPN3, CDAN1, CDAN3, CLN6, CMH3, CYP19, CYP1A1, CYP1A2, DYX1, EPB42, ETFA, EYCL3, FAH, FBN1, FES, HCVS, HEXA, IVD, LCS1, LIPC, MYO5A, OCA2, OTSC1, PWCR, RLBPI, SLC12A1, SPG6, TPM1, UBE3A, WMS, ABCC6, ALDOA, APRT, ATP2A1, BBS2, CARD15, CATM, CDH1, CETP, CHST6, CLN3, CREBBP, CTH, CTM, CYBA, CYLD, DHS, DNASE1, DPEP1, ERCC4, FANCA, GALNS, GAN, HAGH, HBA1, HBA2, HBHR, HBQ1, HBZ, HBZP, HP, HSD11B2, IL4R, LIPB, MC1R, MEFV, MHC2TA, MLYCD, MMVP1, PHKB, PHKG2, PKD1, PKDTS, PMM2, PXE, SALL1, SCA4, SCNN1B, SCNN1G, SLC12A3, TAT, TSC2, VDI, WT3, ABR, ACACA, ACADVL, ACE, ALDH3A2, APOH, ASPA, AXIN2, BCL5, BHD, BLMH, BRCA1, CACD, CCA1, CCZS, CHRNB1, CHRNE, CMT1A, COL1A1, CORD5, CTNS, EPX, ERBB2, G6PC, GAA, GALK1, GCGR, GFAP, GH1, GH2, GP1BA, GPSC, GUCY2D, ITGA2B, ITGB3, ITGB4, KRT10, KRT12, KRT13, KRT14, KRT14L1, KRT14L2, KRT14L3, KRT16, KRT16L1, KRT16L2, KRT17, KRT9, MAPT, MDB, MDCR, MGI, MHS2, MKS1, MPO, MYO15A, NAGLU, NAPB, NF1, NME1, P4HB, PAFAH1B1, PECAM1, PEX12, PHB, PMP22, PRKAR1A, PRKCA, PRKWNK4, PRP8, PRPF8, PTLAH, RARA, RCV1, RMSA1, RP17, RSS, SCN4A, SERPINF2, SGCA, SGSH, SHBG, SLC2A4, SLC4A1, SLC6A4, SMCR, SOST, SOX9, SSTR2, SYM1, SYNS1, TCF2, THRA, TIMP2, TOC, TOP2A, TP53, TRIM37, VBCH, ATP8B1, BCL2, CNSN, CORD1, CYB5, DCC, F5F8D, FECH, FEO, LAMA3, LCFS2, MADH4, MAFD1, MC2R, MCL, MYP2, NPC1, SPPK, TGFBRE, TGIF, TTR, AD2, AMH, APOC2, APOE, ATHS, BAX, BCKDHA, BCL3, BFIC, C3, CACNA1A, CCO, CEACAM5, COMP, CRX, DBA, DDU, DFNA4, DLL3, DM1, DMWD, E11S, ELA2, EPOR, ERCC2, ETFB, EXT3, EYCL1, FTL, FUT1, FUT2, FUT6, GAMT, GCDH, GPI, GUSM, HB1, HCL1, HHC2, HHC3, ICAM3, INSR, JAK3, KLK3, LDLR, LHB, LIG1, LOH19CR1, LYL1, MAN2B1, MCOLN1, MDRV, MLLT1, NOTCH3, NPHS1, OFC3, OPA3, PEPD, PRPF31, PRTN3, PRX, PSG1, PVR, RYR1, SLC5A5, SLC7A9, STK11, TBXA2R, TGFB1, TNNI3, TYROBP, ADA, AHCY, AVP, CDAN2, CDPD1, CHED1, CHED2, CHRNA4, CST3, EDN3, EEGV1, FTLL1, GDF5, GNAS, GSS, HNF4A, JAG1, KCNQ2, MKKS, NBIA1, PCK1, PI3, PPCD, PPGB, PRNP, THBD, TOP1, AIRE, APP, CBS, COL6A1, COL6A2, CSTB, DCR, DSCR1, FPDMM, HLCS, HPE1, ITGB2, KCNE1, KNO, PRSS7, RUNX1, SOD1, TAM, ADSL, ARSA, BCR, CECR, CHEK2, COMT, CRYBB2, CSF2RB, CTHM, CYP2D6, CYP2D7P1, DGCR, DIA1, EWSR1, GGT1, MGCR, MN1, NAGA, NE2, OGS2, PDGFB, PPARA, PRODH, SCO2, SCZD4, SERPIND1, SLC5A1, SOX10, TCN2, TIMP3, TST, VCF, ABCD1, ACTL1, ADFN, AGMX2, AHDS, AIC, AIED, AIH3, ALAS2, AMCD, AMELX, ANOP1, AR, ARAF1, ARSC2, ARSE, ARTS, ARX, ASAT, ASSP5, ATP7A, ATRX, AVPR2, BFLS, BGN, BTK, BZX, C1HR, CACNA1F, CALB3, CBBM, CCT, CDR1, CFNS, CGF1, CHM, CHR39c, CIDX, CLA2, CLCN5, CLS, CMTX2, CMTX3, CND, COD1, COD2, COL4A5, COL4A6, CPX, CVD1, CYBB, DCX, DFN2, DFN4, DFN6, DHOF, DIAPH2, DKC1, DMD, DSS, DYT3, EBM, EBP, ED1, ELK1, EMD, EVR2, F8, F9, FCP1, FDPSL5, FGD1, FGS1, FMR1, FMR2, G6PD, GABRA3, GATA1, GDI1, GDXY, GJB1, GK, GLA, GPC3, GRPR, GTD, GUST, HMS1, HPRT1, HPT, HTC2, HTR2c, HYR, IDS, IHG1, IL2RG, INDX, IP1, IP2, JMS, KAL1, KFSD, L1CAM, LAMP2, MAA, MAFD2, MAOA, MAOB, MCF2, MCS, MEAX, MECP2, MF4, MGC1, MICS, MID1, MLLT7, MLS, MRSD, MRX14, MRX1, MRX20, MRX2, MRX3, MRX40, MRXA, MSD, MTM1, MYCL2, MYP1, NDP, NHS, NPHL1, NROB1, NSX, NYS1, NYX, OA1, OASD, OCRL, ODT1, OFD1, OPA2, OPD1, OPEM, OPN1LW, OPN1MW, OTC, P3, PDHA1, PDR, PFC, PFKFB1, PGK1, PGK1P1, PGS, PHEX, PHKA1, PHKA2, PHP, PIGA, PLP1, POF1, POLA, POU3F4, PPMX, PRD, PRPS1, PRPS2, PRS, RCCP2, RENBP, RENS1, RP2, RP6, RPGR, RPS4X, RPS6KA3, RS1, S11, SDYS, SEDL, SERPINA7, SH2D1A, SHFM2, SLC25A5, SMAX2, SRPX, SRS, STS, SYN1, SYP, TAF1, TAZ, TBX22, TDD, TFE3, THAS, THC, TIMM8A, TIM1, TKCR, TNFSF5, UBE1, UBE2A, WAS, WSN, WTS, WWS, XIC, XIST, XK, XM, XS, ZFX, ZIC3, ZNF261, ZNF41, ZNF6, AMELY, ASSP6, AZF1, AZF2, DAZ, GCY, RPS4Y, SMCY, ZFY, ABAT, AEZ, AFA, AFD1, ASAH1, ASD1, ASMT, CCAT, CECR9, CEPA, CLA3, CLN4, CSF2RA, CTS1, DF, DIH1, DWS, DYT2, DYT4, EBR3, ECT, EEF1A1L14, EYCL2, FANCB, GCSH, GCSL, GIP, GTS, HHG, HMI, HOAC, HOKPP2, HRPT1, HSD3B3, HTC1, HV1S, ICHQ, ICR1, ICR5, IL3RA, KAL2, KMS, KRT18, KSS, LCAT, LHON, LIMM, MANBB, MCPH2, MEB, MELAS, MIC2, MPFD, MS, MSS, MTATP6, MTCO1, MTCO3, MTCYB, MTND1, MTND2, MTND4, MTND5, MTND6, MTRNR1, MTRNR2, MTTE, MTTG, MTTI, MTTK, MTTL1, MTTL2, MTTN, MTTP, MTTS1, NAMSD, OCD1, OPD2, PCK2, PCLD, PCOS1, PFKM, PKD3, PRCA1, PRO1, PROP1, RBS, RFXAP, RP, SHOX, SLC25A6, SPG5B, STO, SUOX, THM, TTD and antibodies. In more specific embodiments, the antibody is selected from the group consisting of anti-interleukin-1 β antibody (see, canakinumab; Ilaris®; EP1313769B2 (Novartis AG); U.S. Pat. No. 7,446, 175 (Gram et al.) and U.S. Pat. No. 8,409,576 (Lowe et al.); CHEMBL1201834; Dhimolea, "Canakinumab". MAbs 2 (1): 3-13 (2010)) and anti-YFV antibody (e.g., 2D12, Schlesinger et al. "Monoclonal antibodies distinguish between wild and vaccine strains of yellow fever virus by neutralization, hemagglutination inhibition, and immune precipitation of the virus envelope protein." Virology 125: 8-17 (1983)).

In a thirty-fifth embodiment, the invention is the method according to the twenty-second embodiment, wherein said mammalian cell is a cell selected from the group consisting of an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, and a zymogenic cell.

In a thirty-sixth embodiment, the invention is the method according to the twenty-second embodiment, wherein said mammalian cell is present in vivo in a mammal In a thirty-seventh embodiment, the invention is the method according to the twenty-second embodiment, wherein said modified messenger RNA is introduced into a mammal; said modified messenger RNA is taken up by a cell of said mammal; and said protein of interest is translated from said modified messenger RNA by said mammalian cell.

In a thirty-eighth embodiment, the invention is the method according to the thirty-third embodiment, wherein said encapsulated modified messenger RNA is introduced into a mammal, said encapsulated modified messenger RNA is taken up by a cell of said mammal, and said protein of interest is translated from said modified messenger RNA by said mammalian cell.

In a thirty-ninth embodiment, the invention is the method according to the twenty-second embodiment, wherein said in messenger RNA is synthesized by in vitro transcription in a reaction mixture comprising a triphosphate derivative of said at least one modified nucleoside selected from the group consisting of

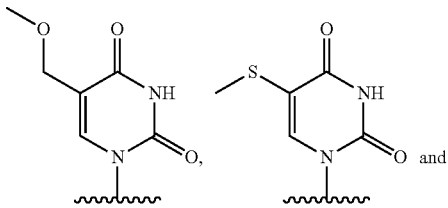

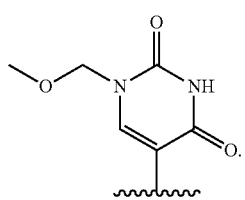 [SMILES: *c1cn(COC)c(=O)[nH]c1=O]

In a fortieth embodiment, the invention is the method according to the twenty-second embodiment, wherein said in vitro-synthesized modified messenger RNA further comprises a modified nucleoside selected from the group consisting of 5-methylcytidine ($m^5C$), pseudouridine ($\Psi$), 1-methypseudouridine ($m^1\Psi$), 5-methyluridine ($m^5U$), $N^6$-methyladenosine ($m^6A$), 2-thiouridine ($S^2U$) and 2'-O-methyluridine (2'-O-methyl-U).

In a forty-first embodiment, the invention is the method according to the fortieth embodiment, wherein said modified messenger RNA exhibits a detectable decrease in immunogenicity to said mammalian cell compared to the same quantity of an unmodified RNA having the same sequence.

In a forty-second embodiment, the invention is the method according to the thirty-ninth embodiment, wherein said reaction mixture comprises a triphosphate derivatives of a modified nucleoside selected from the group consisting of 5-methylcytidine ($m^5C$), pseudouridine ($\Psi$), 1-methypseudouridine ($m^1\Psi$), 5-methyluridine ($m^5U$), $N^6$-methyladenosine ($m^6A$), 2-thiouridine ($S^2U$) and 2'-O-methyluridine (2'-O-methyl-U), and a triphosphate derivatives of said at least one modified nucleoside selected from the group consisting of

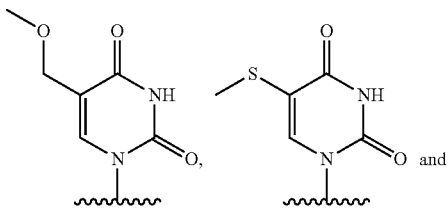

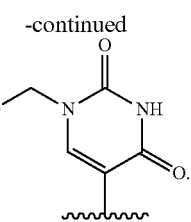

In a forty-third embodiment, the invention is the method according to the fortieth embodiment, wherein said protein of interest comprises a protein selected from the group consisting of erythropoietin (EPO), a detectable enzyme selected from firefly luciferase, Renilla luciferase, bacterial beta-galactosidase (lacZ), green fluorescent protein (GFP), MYC, SRY, MCOP, platelet-derived growth factor (PDGF), vascular endothelial growth factor (VEGF), transforming growth factor-beta1 (TGF-beta1), insulin-like growth factor (IGF), alpha-melanocyte-stimulating hormone (alpha-MSH), insulin-like growth factor-I (IGF-I), IL-4, IL-13, IL-10, inducible nitric oxide synthase (iNOS), a heat shock protein, cystic fibrosis transmembrane conductance regulator (CFTR), an enzyme with antioxidant activity, catalase, phospholipid hydroperoxide glutathione peroxidase, superoxide dismutase-1, superoxide dismutase-2, Bruton's tyrosine kinase, adenosine deaminase, ecto-nucleoside triphosphate diphosphydrolase, ABCA4, ABCD3, ACADM, AGL, AGT, ALDH4A1, ALPL, AMPD1, APOA2, AVSD1, BRCD2, C1QA, C1QB, C1QG, C8A, C8B, CACNA1S, CCV, CD3Z, CDC2L1, CHML, CHS1, CIAS1, CLCNKB, CMD1A, CMH2, CMM, COL11A1, COL8A2, COL9A2, CPT2, CRB1, CSE, CSF3R, CTPA, CTSK, DBT, DIO1, DISC1, DPYD, EKV, ENO1, ENO1P, EPB41, EPHX1, F13B, F5, FCGR2A, FCGR2B, FCGR3A, FCHL, FH, FMO3, FMO4, FUCA1, FY, GALE, GBA, GFND, GJA8, GJB3, GLC3B, HF1, HMGCL, HPC1, HRD, HRPT2, HSD3B2, HSPG2, KCNQ4, KCS, KIF1B, LAMB3, LAMC2, LGMD1B, LMNA, LOR, MCKD1, MCL1, MPZ, MTHFR, MTR, MUTYH, MYOC, NB, NCF2, NEM1, NPHS2, NPPA, NRAS, NTRK1, OPTA2, PBX1, PCHC, PGD, PHA2A, PHGDH, PKLR, PKP1, PLA2G2A, PLOD, PPDX, PPTO, PRCC, PRG4, PSEN2, PTOS1, REN, RFX5, RHD, RMD1, RPE65, SCCD, SERPINC1, SJS1, SLC19A2, SLC2A1, SPG23, SPTA1, TAL1, TNFSF6, TNNT2, TPM3, TSHB, UMPK, UOX, UROD, USH2A, VMGLOM, VWS, WS2B, ABCB11, ABCG5, ABCG8, ACADL, ACP1, AGXT, AHHR, ALMS1, ALPP, ALS2, APOB, BDE, BDMR, BJS, BMPR2, CHRNA1, CMCWTD, CNGA3, COL3A1, COLAA3, COL4A4, COL6A3, CPS1, CRYGA, CRYGEP1, CYP1B1, CYP27A1, DBI, DES, DYSF, EDAR, EFEMP1, EIF2AK3, ERCC3, FSHR, GINGF, GLC1B, GPD2, GYPC, HADHA, HADHB, HOXD13, HPE2, IGKC, IHH, IRS1, ITGA6, KHK, KYNU, LCT, LHCGR, LSFC, MSH2, MSH6, NEB, NMTC, NPHP1, PAFAH1P1, PAX3, PAX8, PMS1, PNKD, PPH1, PROC, REG1A, SAG, SFTPB, SLC11A1, SLC3A1, SOS1, SPG4, SRD5A2, TCL4, TGFA, TMD, TPO, UGT1A@, UV24, WSS, XDH, ZAP70, ZFHX1B, ACAA1, AGS1, AGTR1, AHSG, AMT, ARMET, BBS3, BCHE, BCPM, BTD, CASR, CCR2, CCR5, CDL1, CMT2B, COL7A1, CP, CPO, CRV, CTNNB1, DEM, ETM1, FANCD2, FIH, FOXL2, GBE1, GLB1, GLCLC, GNAI2, GNAT1, GP9, GPX1, HGD, HRG, ITIH1, KNG, LPP, LRS1, MCCC1, MDS1, MHS4, MITF, MLH1, MYL3, MYMY, OPA1, P2RY12, PBXP1, PCCB, POU1F1, PPARG, PROS1, PTHR1, RCA1, RHO, SCA7, SCLC1, SCN5A, SI, SLC25A20, SLC2A2, TF, TGFBR2, THPO, THRB, TKT, TM4SF1, TRH, UMPS, UQCRC1, USH3A, VHL, WS2A, XPC, ZNF35, ADH1B, ADH1C, AFP, AGA, AIH2, ALB, ASMD, BFHD, CNGA1, CRBM, DCK, DSPP, DTDP2, ELONG, ENAM, ETFDH, EVC, F11, FABP2, FGA, FGB, FGFR3, FGG, FSHMDIA, GC, GNPTA, GNRHR, GYPA, HCA, HCL2, HD, HTN3, HVBS6, IDUA, IF, JPD, KIT, KLKB1, LQT4, MANBA, MLLT2, MSX1, MTP, NR3C2, PBT, PDE6B, PEE1, PITX2, PKD2, QDPR, SGCB, SLC25A4, SNCA, SOD3, STATH, TAPVR1, TYS, WBS2, WFS1, WHCR, ADAMTS2, ADRB2, AMCN, AP3B1, APC, ARSB, B4GALT7, BHR1, C6, C7, CCAL2, CKN1, CMDJ, CRHBP, CSF1R, DHFR, DIAPH1, DTR, EOS, EPD, ERVR, F12, FBN2, GDNF, GHR, GLRA1, GM2A, HEXB, HSD17B4, ITGA2, KFS, LGMDLA, LOX, LTC4S, MAN2A1, MCC, MCCC2, MSH3, MSX2, NR3C1, PCSK1, PDE6A, PFBI, RASA1, SCZD1, SDHA, SGCD, SLC22A5, SLC26A2, SLC6A3, SM1, SMA@, SMN1, SMN2, SPINK5, TCOF1, TELAB1, TGFBI, ALDH5A1, ARG1, AS, ASSP2, BCKDHB, BF, C2, C4A, CDKN1A, COL10A1, COL11A2, CYP21A2, DYX2, EJM1, ELOVL4, EPM2A, ESR1, EYA4, F13A1, FANCE, GCLC, GJA1, GLYS1, GMPR, GSE, HCR, HFE, HLA-A, HLA-DPB1, HLA-DRA, HPFH, ICS1, IDDM1, IFNGR1, IGAD1, IGF2R, ISCW, LAMA2, LAP, LCA5, LPA, MCDR1, MOCS1, MUT, MYB, NEU1, NKS1, NYS2, OA3, ODDD, OFC0, PARK2, PBCA, PBCRA1, PDB1, PEX3, PEX6, PEX7, PKHD1, PLA2G7, PLG, POLH, PPAC, PSORS1, PUJO, RCD1, RDS, RHAG, RP14, RUNX2, RWS, SCA1, SCZD3, SIASD, SOD2, ST8, TAP1, TAP2, TFAP2B, TNDM, TNF, TPBG, TPMT, TULP1, WISP3, AASS, ABCB1, ABCB4, ACHE, AQP1, ASL, ASNS, AUTS1, BPGM, BRAF, C7orf2, CACNA2D1, CCM1, CD36, CFTR, CHORDOMA, CLCN1, CMH6, CMT2D, COL1A2, CRS, CYMD, DFNA5, DLD, DYT11, EEC1, ELN, ETV1, FKBP6, GCK, GHRHR, GHS, GLI3, GPDS1, GUSB, HLXB9, HOXA13, HPFH2, HRX, IAB, IMMP2L, KCNH2, LAMB1, LEP, MET, NCF1, NM, OGDH, OPN1SW, PEX1, PGAM2, PMS2, PON1, PPP1R3A, PRSS1, PTC, PTPN12, RP10, RP9, SERPTNE1, SGCE, SHFM1, SHH, SLC26A3, SLC26A4, SLOS, SMAD1, TBXAS1, TWIST, ZWS1, ACHM3, ADRB3, ANK1, CA1, CA2, CCAL1, CLN8, CMT4A, CNGB3, COH1, CPP, CPN, CYP11B1, CYP11B2, DECR1, DPYS, DURS1, EBS1, ECA1, EGI, EXT1, EYA1, FGFR1, GNRH1, GSR, GULOP, HR, KCNQ3, KFM, KWE, LGCR, LPL, MCPH1, MOS, MYC, NAT1, NAT2, NBS1, PLAT, PLEC1, PRKDC, PXMP3, RP1, SCZD6, SFTPC, SGM1, SPG5A, STAR, TG, TRPS1, TTPA, VMD1, WRN, ABCA1, ABL1, ABO, ADAMTS13, AK1, ALAD, ALDH1A1, ALDOB, AMBP, AMCD1, ASS, BDMF, BSCL, C5, CDKN2A, CHAC, CLA1, CMD1B, COL5A1, CRAT, DBH, DNAI1, DYS, DYT1, ENG, FANCC, FBP1, FCMD, FRDA, GALT, GLDC, GNE, GSM1, GSN, HSD17B3, HSN1, IBM2, INVS, JBTS1, LALL, LCCS1, LCCS, LGMD2H, LMX1B, MLLT3, MROS, MSSE, NOTCH1, ORM1, PAPPA, PIP5K1B, PTCH, PTGS1, RLN1, RLN2, RMRP, ROR2, RPD1, SARDH, SPTLC1, STOM, TDFA, TEK, TMC1, TRIM32, TSC1, TYRP1, XPA, CACNB2, COL17A1, CUBN, CXCL12, CYP17, CYP2C19, CYP2C9, EGR2, EMX2, ERCC6, FGFR2, HK1, HPS1, IL2RA, LGI1, LIPA, MAT1A, MBL2, MKI67, MXI1, NODAL, OAT, OATL3, PAX2, PCBD, PEO1, PHYH, PNLIP, PSAP, PTEN, RBP4, RDPA, RET, SFTPA1, SFTPD, SHFM3, SIAL, THC2, TLX1, TNFRSF6, UFS, UROS, AA, ABCB8, ACAT1, ALX4, AMPD3, ANC, APOAL, APOA4, APOC3, ATM, BSCL2, BWS, CALCA, CAT, CCND1, CD3E, CD3G, CD59, CDKNLC, CLN2, CNTF, CPT1A, CTSC, DDB1, DDB2, DHCR7, DLAT, DRD4, ECB2, ED4, EVR1, EXT2, F2, FSHB, FTH1, G6PT1, G6PT2, GIF, HBB, HBBP1, HBD, HBE1, HBG1, HBG2, HMBS, HND, HOMG2, HRAS, HVBS1, IDDM2, IGER, INS, JBS, KCNJ11, KCNJ1, KCNQ1, LDHA, LRP5, MEN1, MLL, MYBPC3, MYO7A, NNO1, OPPG, OPTB1, PAX6, PC, PDX1, PGL2, PGR, PORC, PTH, PTS, PVRL1, PYGM, RAG1, RAG2, ROM1, RRAS2, SAA1, SCA5, SCZD2, SDHD, SERPING1, SMPD1, TCIRG1, TCL2, TECTA, TH, TREH, TSG101, TYR, USHIC, VMD2, VRNI, WT1, WT2, ZNF145, A2M, AAAS, ACADS, ACLS, ACVRL1, ALDH2, AMHR2, AOM, AQP2, ATD, ATP2A2, BDC, CIR, CD4, CDK4, CNA1, COL2A1, CYP27B1, DRPLA, ENUR2, FEOM1, FGF23, FPF, GNB3, GNS, HAL, HBP1, HMGA2, HMN2, HPD, IGF1, KCNA1, KERA, KRAS2, KRT1, KRT2A, KRT3, KRT4, KRT5, KRT6A, KRT6B, KRTHB6, LDHB, LYZ, MGCT, MPE, MVK, MYL2, OAP, PAH, PPKB, PRB3, PTPN11, PXR1, RLS, RSN, SAS, SAX1, SCA2, SCNN1A, SMAL, SPPM, SPSMA, TBX3, TBX5, TCF1, TPI1, TSC3, ULR, VDR, VWF, ATP7B, BRCA2, BRCD1, CLN5, CPB2, ED2, EDNRB, ENUR1, ERCC5, F10, F7, GJB2, GJB6, IPF1, MBS1, MCOR, NYS4, PCCA, RB1, RHOK, SCZD7, SGCG, SLC10A2, SLC25A15, STARP1, ZNF198, ACHM1, ARVD1, BCH, CTAA1, DAD1, DFNB5, EML1, GALC, GCH1, IBGC1, IGH@, IGHC group, IGHG1, IGHM, IGHR, IV, LTBP2, MJD, MNG1, MPD1, MPS3C, MYH6, MYH7, NP, NPC2, PABPN1, PSEN1, PYGL, RPGRIP1, SERPINA1, SERPINA3, SERPINA6, SLC7A7, SPG3A, SPTB, TCL1A, TGM1, TITF1, TMIP, TRA@, TSHR, USHLA, VP, ACCPN, AHO2, ANCR, B2M, BBS4, BLM, CAPN3, CDAN1, CDAN3, CLN6, CMH3, CYP19, CYP1A1, CYP1A2, DYX1, EPB42, ETFA, EYCL3, FAH, FBN1, FES, HCVS, HEXA, IVD, LCS1, LIPC, MYO5A, OCA2, OTSC1, PWCR, RLBP1, SLC12A1, SPG6, TPM1, UBE3A, WMS, ABCC6, ALDOA, APRT, ATP2A1, BBS2, CARD15, CATM, CDH1, CETP, CHST6, CLN3, CREBBP, CTH, CTM, CYBA, CYLD, DHS, DNASE1, DPEP1, ERCC4, FANCA, GALNS, GAN, HAGH, HBA1, HBA2, HBHR, HBQ1, HBZ, HBZP, HP, HSD11B2, IL4R, LIPB, MC1R, MEFV, MHC2TA, MLYCD, MMVP1, PHKB, PHKG2, PKD1, PKDTS, PMM2, PXE, SALL1, SCA4, SCNN1B, SCNN1G, SLC12A3, TAT, TSC2, VDI, WT3, ABR, ACACA, ACADVL, ACE, ALDH3A2, APOH, ASPA, AXIN2, BCL5, BHD, BLMH, BRCA1, CACD, CCA1, CCZS, CHRNB1, CHRNE, CMT1A, COL1A1, CORD5, CTNS, EPX, ERBB2, G6PC, GAA, GALK1, GCGR, GFAP, GH1, GH2, GP1BA, GPSC, GUCY2D, ITGA2B, ITGB3, ITGB4, KRT10, KRT12, KRT13, KRT14, KRT14L1, KRT14L2, KRT14L3, KRT16, KRT16L1, KRT16L2, KRT17, KRT9, MAPT, MDB, MDCR, MGI, MHS2, MKS1, MPO, MYO15A, NAGLU, NAPB, NF1, NME1, P4HB, PAFAH1B1, PECAM1, PEX12, PHB, PMP22, PRKAR1A, PRKCA, PRKWNK4, PRP8, PRPF8, PTLAH, RARA, RCV1, RMSA1, RP17, RSS, SCN4A, SERPINF2, SGCA, SGSH, SHBG, SLC2A4, SLC4A1, SLC6A4, SMCR, SOST, SOX9, SSTR2, SYM1, SYNS1, TCF2, THRA, TIMP2, TOC, TOP2A, TP53, TRIM37, VBCH, ATP8B1, BCL2, CNSN, CORD1, CYB5, DCC, F5F8D, FECH, FEO, LAMA3, LCFS2, MADH4, MAFD1, MC2R, MCL, MYP2, NPC1, SPPK, TGFBRE, TGIF, TTR, AD2, AMH, APOC2, APOE, ATHS, BAX, BCKDHA, BCL3, BFIC, C3, CACNA1A, CCO, CEACAM5, COMP, CRX, DBA, DDU, DFNA4, DLL3, DM1, DMWD, E11S, ELA2, EPOR, ERCC2, ETFB, EXT3, EYCL1, FTL, FUT1, FUT2, FUT6, GAMT, GCDH, GPI, GUSM, HB1, HCL1, HHC2, HHC3, ICAM3, INSR, JAK3, KLK3, LDLR, LHB, LIG1, LOH19CR1, LYL1, MAN2B1, MCOLN1, MDRV, MLLT1, NOTCH3, NPHS1, OFC3, OPA3, PEPD, PRPF31, PRTN3, PRX, PSG1, PVR, RYR1, SLC5A5, SLC7A9, STK11, TBXA2R, TGFB1, TNNI3, TYROBP, ADA, AHCY, AVP, CDAN2, CDPD1, CHED1, CHED2, CHRNA4, CST3, EDN3, EEGV1, FTLL1, GDF5, GNAS, GSS, HNF4A, JAG1, KCNQ2, MKKS, NBIA1, PCK1, PI3, PPCD, PPGB, PRNP, THBD, TOP1, AIRE, APP, CBS, COL6A1, COL6A2, CSTB, DCR, DSCR1, FPDMM, HLCS, HPE1, ITGB2, KCNE1, KNO, PRSS7, RUNX1, SOD1, TAM, ADSL, ARSA, BCR, CECR, CHEK2, COMT, CRYBB2, CSF2RB, CTHM, CYP2D6, CYP2D7P1, DGCR, DIA1, EWSR1, GGT1, MGCR, MN1, NAGA, NE2, OGS2, PDGFB, PPARA, PRODH, SCO2, SCZD4, SERPIND1, SLC5A1, SOX10, TCN2, TIMP3, TST, VCF, ABCD1, ACTL1, ADFN, AGMX2, AHDS, AIC, AIED, AIH3, ALAS2, AMCD, AMELX, ANOP1, AR, ARAF1, ARSC2, ARSE, ARTS, ARX, ASAT, ASSP5, ATP7A, ATRX, AVPR2, BFLS, BGN, BTK, BZX, C1HR, CACNA1F, CALB3, CBBM, CCT, CDR1, CFNS, CGF1, CHM, CHR39c, CIDX, CLA2, CLCN5, CLS, CMTX2, CMTX3, CND, COD1, COD2, COL4A5, COL4A6, CPX, CVD1, CYBB, DCX, DFN2, DFN4, DFN6, DHOF, DIAPH2, DKC1, DMD, DSS, DYT3, EBM, EBP, ED1, ELK1, EMD, EVR2, F8, F9, FCP1, FDPSL5, FGD1, FGS1, FMR1, FMR2, G6PD, GABRA3, GATA1, GDI1, GDXY, GJB1, GK, GLA, GPC3, GRPR, GTD, GUST, HMS1, HPRT1, HPT, HTC2, HTR2c, HYR, IDS, IHG1, IL2RG, INDX, IP1, IP2, JMS, KAL1, KFSD, L1CAM, LAMP2, MAA, MAFD2, MAOA, MAOB, MCF2, MCS, MEAX, MECP2, MF4, MGC1, MICS, MID1, MLLT7, MLS, MRSD, MRX14, MRX1, MRX20, MRX2, MRX3, MRX40, MRXA, MSD, MTM1, MYCL2, MYP1, NDP, NHS, NPHL1, NROB1, NSX, NYS1, NYX, OA1 OASD, OCRL, ODT1, OFD1, OPA2, OPD1, OPEM, OPN1LW, OPN1MW, OTC, P3, PDHA1, PDR, PFC, PFKFB1, PGK1, PGK1P1, PGS, PHEX, PHKA1, PHKA2, PHP, PIGA, PLP1, POF1, POLA, POU3F4, PPMX, PRD, PRPS1, PRPS2, PRS, RCCP2, RENBP, RENS1, RP2, RP6, RPGR, RPS4X, RPS6KA3, RS1, S11, SDYS, SEDL, SERPINA7, SH2D1A, SHFM2, SLC25A5, SMAX2, SRPX, SRS, STS, SYN1, SYP, TAF1, TAZ, TBX22, TDD, TFE3, THAS, THC, TIMM8A, TIM1, TKCR, TNFSFS, UBE1, UBE2A, WAS, WSN, WTS, WWS, XIC, XIST, XK, XM, XS, ZFX, ZIC3, ZNF261, ZNF41, ZNF6, AMELY, ASSP6, AZF1, AZF2, DAZ, GCY, RPS4Y, SMCY, ZFY, ABAT, AEZ, AFA, AFD1, ASAH1, ASD I, ASMT, CCAT, CECR9, CEPA, CLA3, CLN4, CSF2RA, CTS1, DF, DIH1, DWS, DYT2, DYT4, EBR3, ECT, EEF1A1L14, EYCL2, FANCB, GCSH, GCSL, GIP, GTS, HHG, HMI, HOAC, HOKPP2, HRPT1, HSD3B3, HTC1, HV1S, ICHQ, ICR1, ICR5, IL3RA, KAL2, KMS, KRT18, KSS, LCAT, LHON, LIMM, MANBB, MCPH2, MEB, MELAS, MIC2, MPFD, MS, MSS, MTATP6, MTCO1, MTC03, MTCYB, MTND1, MTND2, MTND4, MTND5, MTND6, MTRNR1, MTRNR2, MTTE, MTTG, MTTI, MTTK, MTTL1, MTTL2, MTTN, MTTP, MTTS1, NAMSD, OCD1, OPD2, PCK2, PCLD, PCOS1, PFKM, PKD3, PRCA1, PRO1, PROP1, RBS, RFXAP, RP, SHOX, SLC25A6, SPG5B, STO, SUOX, TIIM, TTD and antibodies. In more specific embodiments, the antibody is selected from the group consisting of anti-interleukin-1 β antibody (see, canakinumab; Ilaris®; EP1313769B2 (Novartis AG); U.S. Pat. No. 7,446,175 (Gram et al.) and U.S. Pat. No. 8,409,576 (Lowe et al.); CHEMBL1201834; Dhimolea, "Canakinumab". MAbs 2 (1): 3-13 (2010)) and anti-YFV antibody (e.g., 2D12, Schlesinger et al. "Monoclonal antibodies distinguish between wild and vaccine strains of yellow fever virus by neutralization, hemagglutination inhibition, and immune precipitation of the virus envelope protein." Virology 125: 8-17 (1983)).

In a forty-fourth embodiment, the invention is the method according to the fortieth embodiment, wherein said mammalian cell is a cell selected from the group consisting of an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, and a zymogenic cell.

In a forty-fifth embodiment, the invention is the method according to the fortieth embodiment, wherein said mammalian cell is present in vivo in a mammal.

In a forty-sixth embodiment, the invention is a method of treating a condition in a mammal caused by a deficiency of a protein of interest, comprising: administering a therapeutically effective amount of a modified messenger RNA comprising an open reading frame that encodes the protein of interest, wherein said modified RNA comprises a modified nucleoside selected from the group consisting of:

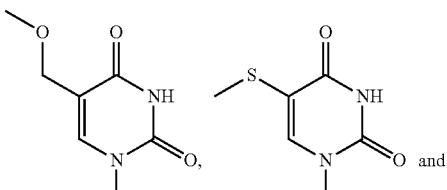

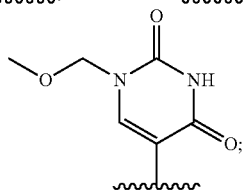

wherein said modified messenger RNA is taken up by a cell of said mammal, and said protein of interest is translated from said modified messenger RNA by said mammalian cell; thereby relieving said condition in said mammal.

In a forty-seventh embodiment, the invention is the method according to the forty-sixth embodiment, wherein the mammal is a human.

In a forty-eighth embodiment, the invention is the method according to the forty-sixth embodiment, wherein said in vitro-synthesized modified messenger RNA is encapsulated in a nanoparticle, polymer, lipid, cholesterol, or a cell penetrating peptide.

In a forty-ninth embodiment, the invention is the method according to the forty-sixth embodiment, wherein the condition is anemia and the protein of interest is erythropoietin EPO.

In a fiftieth embodiment, the invention is the method according to the forty-sixth embodiment, wherein the condition is obesity and the protein of interest is leptin (LEP).

In a fifty-first embodiment, the invention is the method according to the forty-sixth embodiment, wherein said modified messenger RNA induces a detectably lower innate immune response than the same quantity of a corresponding unmodified messenger RNA.

In a fifty-second embodiment, the invention is the method according to the forty-sixth embodiment, wherein said modified messenger RNA further comprises a modified nucleoside selected from the group consisting of 5-methylcytidine ($m^5C$), pseudouridine ($\Psi$), 1-methypseudouridine ($m^1\Psi$), 5-methyluridine ($m^5U$), $N^6$-methyladenosine ($m^6A$), 2-thiouridine ($S^2U$) and 2'-O-methyluridine (2'-O-methyl-U).

In one embodiment, the invention is the method according to any of the preceding embodiments, wherein the messenger RNA comprises the nucleoside:

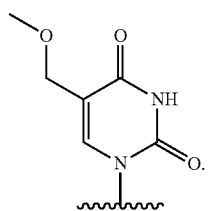 [SMILES: *n1cc(COC)c(=O)[nH]c1=O]

In another embodiment, the invention is the method according to any of the preceding embodiments, wherein the messenger RNA comprises the nucleoside:

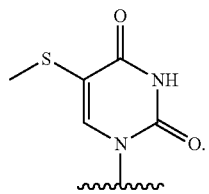 [SMILES: *n1cc(SC)c(=O)[nH]c1=O]

In yet another embodiment, the invention is the method according to any of the preceding embodiments, wherein the messenger RNA comprises the nucleoside:

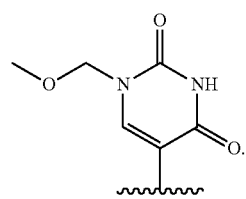

This invention provides modified messenger RNA comprising an open reading frame that encodes a protein of interest, wherein said modified messenger RNA comprises a modified nucleoside selected from the group consisting of:

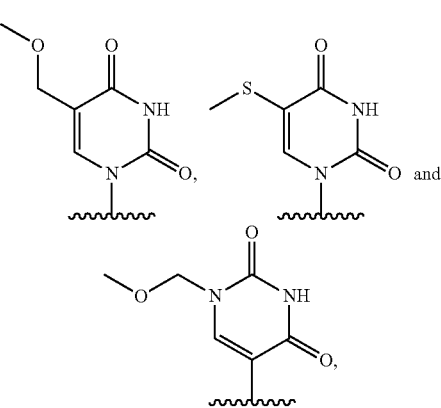

gene therapy vectors comprising same, gene therapy methods and gene transcription silencing methods comprising same, methods of reducing an immunogenicity of same, and methods of synthesizing same.

In one embodiment, the present invention provides a modified messenger RNA comprising an open reading frame that encodes a protein of interest, wherein said modified messenger RNA comprises a modified nucleoside selected from the group consisting of:

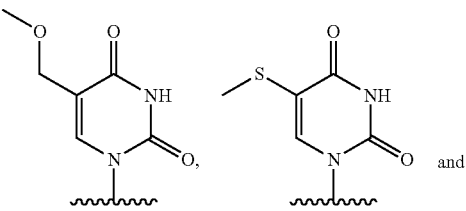

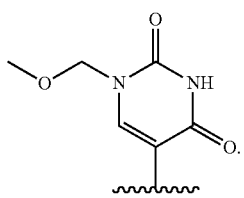

In another embodiment, the messenger RNA encodes a protein of interest. Each possibility represents a separate embodiment of the present invention.

In another embodiment, the present invention provides a modified mRNA molecule encoding a protein of interest, said modified mRNA molecule comprises a modified nucleoside selected from the group consisting of:

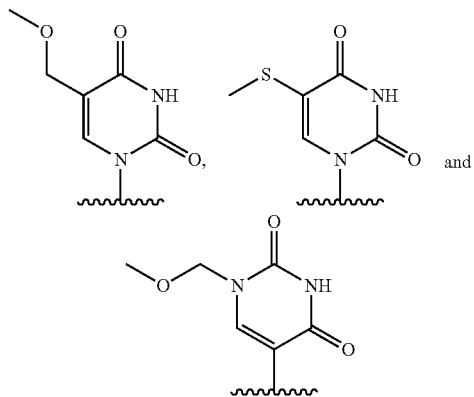

residue.

In another embodiment, the present invention provides in vitro-transcribed modified mRNA molecule, comprises a modified nucleoside selected from the group consisting of:

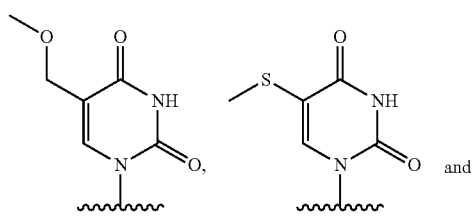

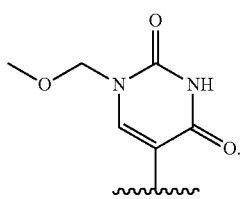 [SMILES: *c1cn(COC)c(=O)[nH]c1=O]

As provided herein, the present invention provides methods for synthesizing in vitro-transcribed modified mRNA molecules, comprising a modified nucleoside selected from the group consisting of:

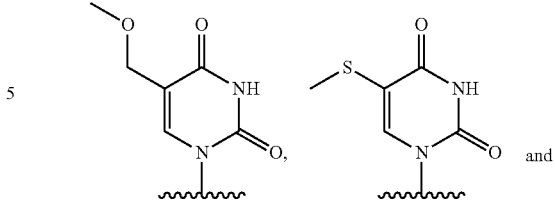

In another embodiment, the modified mRNA further comprises a poly-A tail. In another embodiment, the modified mRNA does not comprise a poly-A tail. Each possibility represents a separate embodiment of the present invention.

In another embodiment, the modified mRNA further comprises an m7 GpppG cap. In another embodiment, the modified mRNA does not comprise an m7 GpppG cap. Each possibility represents a separate embodiment of the present invention.

In another embodiment, the modified mRNA further comprises a cap-independent translational enhancer. In another embodiment, the modified mRNA does not comprise a cap-independent translational enhancer. In another embodiment, the cap-independent translational enhancer is a tobacco etch virus (TEV) cap-independent translational enhancer. In another embodiment, the cap-independent translational enhancer is any other cap-independent translational enhancer known in the art. Each possibility represents a separate embodiment of the present invention.

"Pseudouridine" refers, in another embodiment, to $m^1acp^3\Psi$ (1-methyl-3-(3-amino-5-carboxypropyl)pseudouridine). In another embodiment, the term refers to $m^1\Psi$ (1-methylpseudouridine). In another embodiment, the term refers to $\Psi m$ (2'-O-methylpseudouridine.

In another embodiment, the term refers to $m^5D$ (5-methyldihydrouridine). In another embodiment, the term refers to $m^3\Psi$ (3-methylpseudouridine). In another embodiment, the term refers to a pseudouridine moiety that is not further modified. In another embodiment, the term refers to a monophosphate, diphosphate, or triphosphate of any of the above pseudouridines. In another embodiment, the term refers to any other pseudouridine known in the art. Each possibility represents a separate embodiment of the present invention.

In another embodiment, a modified mRNA of methods and compositions of the present invention is a therapeutic modified mRNA.

In another embodiment, the present invention provides a method for delivering a recombinant protein to a subject, the method comprising the step of contacting the subject with a modified mRNA, thereby delivering a recombinant protein to a subject.

In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides. Each possibility represents a separate embodiment of the present invention.

In another embodiment, a modified mRNA of methods and compositions of the present invention is manufactured by in vitro-transcription.

In another embodiment, the nucleoside that is modified in a modified mRNA of methods and compositions of the present invention is uridine (U). In another embodiment, the modified nucleoside is cytidine (C). In another embodiment, the modified nucleoside is adenine (A). In another embodiment the modified nucleoside is guanine (G). Each possibility represents a separate embodiment of the present invention.

In another embodiment, the modified nucleoside of methods and compositions of the present invention is $m^5C$ (5-methylcytidine). In another embodiment, the modified nucleoside is $m^5U$ (5-methyluridine). In another embodiment, the modified nucleoside is $m^6A$ ($N^6$-methyladenosine).

In another embodiment, the modified nucleoside is $s^2U$ (2-thiouridine). In another embodiment, the modified nucleoside is Ψ (pseudouridine). In another embodiment, the modified nucleoside is Um (2'-O-methyluridine).

In other embodiments, the modified nucleoside is $m^1A$ (1-methyladenosine); $m^2A$ (2-methyladenosine); Am (2'-O-methyladenosine); $ms^2 m^6A$ (2-methylthio-$N^6$-methyladenosine); $i^6A$ ($N^6$-isopentenyladenosine); $ms^2i^6A$ (2-methylthio-$N^6$ isopentenyladenosine); $io^6A$ ($N^6$-(cis-hydroxyisopentenyl)adenosine); $ms^2i^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$($N^4$-acetylcytidine); $f^5C$ (5-formylcytidine); $m^5$ Cm (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2_2G$ ($N^2,N^2$-dimethylguanosine); $m^2Gm$ ($N^2,2'$-O-dimethylguanosine); $m^2_2Gm$ ($N^2,N^2,2'$-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$(7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5s^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6_2A$ ($N^6,N^6$-dimethyladenosine); Im (2'-O-methylinosine); $m^4C$($N^4$-methylcytidine); $m^4$ Cm ($N^4,2'$-O-dimethylcytidine); $hm^5C$ (5-hydroxymethylcytidine); $m^3U$ (3-methyluridine); $cm^5U$ (5-carboxymethyluridine); $m^6Am$ ($N^6,2'$-O-dimethyladenosine); $m^6_2Am$ ($N^6,N^6,O$-2'-trimethyladenosine); $m^{2,7}G$ ($N^2,7$-dimethylguanosine); $m^{2,2,7}G$ ($N^2,N^2,7$-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5s^2U$ (5-taurinomethyl-2-thiouridine)); imG-14 (4-demethylwyosine); imG2 (isowyosine); or $ac^6A$ ($N^6$-acetyladenosine). Each possibility represents a separate embodiment of the present invention.

In another embodiment, a modified mRNA of methods and compositions of the present invention comprises a combination of 2 or more of the above modifications. In another embodiment, the modified mRNA comprises a combination of 3 or more of the above modifications. In another embodiment, the modified mRNA comprises a combination of more than 3 of the above modifications. Each possibility represents a separate embodiment of the present invention.

In another embodiment, between 0.1% and 100% of the residues in the modified mRNA of methods and compositions of the present invention are modified (e.g. by the presence of a modified nucleoside selected from the group consisting of:

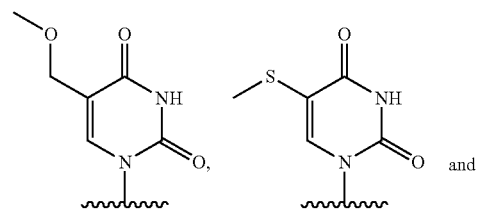

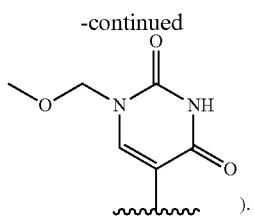

In another embodiment, 0.1% of the residues are modified. In another embodiment, 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.8%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 8%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 60%. In another embodiment, the fraction is 70%. In another embodiment, the fraction is 80%. In another embodiment, the fraction is 90%. In another embodiment, the fraction is 100%.

In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 8%.

In another embodiment, the fraction is less than 10%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%.

In another embodiment, the fraction is less than 60%. In another embodiment, the fraction is less than 70%.

In another embodiment, 0.1% of the residues of a given nucleotide (uridine, cytidine, guanosine, or adenine) are modified. In another embodiment, the fraction of the nucleotide is 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.8%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 8%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 60%. In another embodiment, the fraction is 70%. In another embodiment, the fraction is 80%. In another embodiment, the fraction is 90%. In another embodiment, the fraction is 100%.

In another embodiment, the fraction of the given nucleotide is less than 8%. In another embodiment, the fraction is less than 10%. In another embodiment, the fraction is less than 5%.

In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 12%. In another embodiment, the fraction is less than 15%.

In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, the terms "ribonucleotide," "oligoribonucleotide," and polyribonucleotide refers to a string of at least 2 base-sugar-phosphate combinations. The term includes, in another embodiment, compounds comprising nucleotides in which the sugar moiety is ribose. In another embodiment, the term includes both RNA and RNA derivates in which the backbone is modified. "Nucleotides" refers, in another embodiment, to the monomeric units of nucleic acid polymers. RNA may be, in an other embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). In addition, these forms of RNA may be single, double, triple, or quadruple stranded. The term also includes, in another embodiment, artificial nucleic acids that may contain other types of backbones but the same bases. In another embodiment, the artificial nucleic acid is a PNA (peptide nucleic acid). PNA contain peptide backbones and nucleotide bases and are able to bind, in another embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention In another embodiment, the term "oligoribonucleotide" refers to a string comprising fewer than 25 nucleotides (nt). In another embodiment, "oligoribonucleotide" refers to a string of fewer than 24 nucleotides. In another embodiment, "oligoribonucleotide" refers to a string of fewer than 23 nucleotides. In another embodiment, "oligoribonucleotide" refers to a string of fewer than 22 nucleotides. In another embodiment, "oligoribonucleotide" refers to a string of fewer than 21 nucleotides. In another embodiment, "oligoribonucleotide" refers to a string of fewer than 20 nucleotides. In another embodiment, "oligoribonucleotide" refers to a string of fewer than 19 nucleotides. In another embodiment, "oligoribonucleotide" refers to a string of fewer than 18 nucleotides. In another embodiment, "oligoribonucleotide" refers to a string of fewer than 17 nucleotides. In another embodiment, "oligoribonucleotide" refers to a string of fewer than 16 nucleotides. Each possibility represents a separate embodiment of the present invention.

In another embodiment, the term "polyribonucleotide" refers to a string comprising more than 25 nucleotides (nt). In another embodiment, "polyribonucleotide," refers to a string of more than 26 nucleotides. In another embodiment, "polyribonucleotide" refers to a string of more than 28 nucleotides. In another embodiment, "the term" refers to a string of more than 30 nucleotides. In another embodiment, "the term" refers to a string of more than 32 nucleotides. In another embodiment, "the term" refers to a string of more than 35 nucleotides. In another embodiment, "the term" refers to a string of more than 40 nucleotides. In another embodiment, "the term" refers to a string of more than 50 nucleotides. In another embodiment, "the term" refers to a string of more than 60 nucleotides. In another embodiment, "the term" refers to a string of more than 80 nucleotides. In another embodiment, "the term" refers to a string of more than 100 nucleotides. In another embodiment, "the term" refers to a string of more than 120 nucleotides. In another embodiment, "the term" refers to a string of more than 150 nucleotides. In another embodiment, "the term" refers to a string of more than 200 nucleotides. In another embodiment, "the term" refers to a string of more than 300 nucleotides. In another embodiment, "the term" refers to a string of more than 400 nucleotides. In another embodiment, "the term" refers to a string of more than 500 nucleotides. In another embodiment, "the term" refers to a string of more than 600 nucleotides. In another embodiment, "the term" refers to a string of more than 800 nucleotides. In another embodiment, "the term" refers to a string of more than 1000 nucleotides.

In another embodiment, "the term" refers to a string of more than 1200 nucleotides. In another embodiment, "the term" refers to a string of more than 1400 nucleotides. In another embodiment, "the term" refers to a string of more than 1600 nucleotides. In another embodiment, "the term" refers to a string of more than 1800 nucleotides. In another embodiment, "the term" refers to a string of more than 2000 nucleotides. Each possibility represents a separate embodiment of the present invention.

In another embodiment, the present invention provides a method for inducing a mammalian cell to produce a protein of interest, comprising contacting the mammalian cell with an in vitro-synthesized RNA molecule encoding the recombinant protein, the in vitro-synthesized modified mRNA molecule comprising a modified nucleoside selected from the group consisting of:

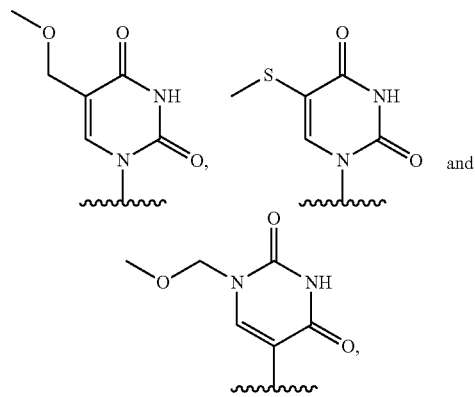

thereby inducing a mammalian cell to produce a protein of interest. In another embodiment, the protein of interest is a recombinant protein. Each possibility represents a separate embodiment of the present invention. "Encoding" refers, in another embodiment, to an RNA molecule that contains a gene that encodes the protein of interest. In another embodiment, the RNA molecule comprises an open reading frame that encodes the protein of interest. In another embodiment, 1 or more other proteins is also encoded. In another embodiment, the protein of interest is the only protein encoded. Each possibility represents a separate embodiment of the present invention.

In another embodiment, the present invention provides a method of inducing a mammalian cell to produce a recombinant protein, comprising contacting the mammalian cell with an in vitro-transcribed RNA molecule encoding the recombinant protein, the in vitro-transcribed modified mRNA molecule further comprising a modified nucleoside selected from the group consisting of:

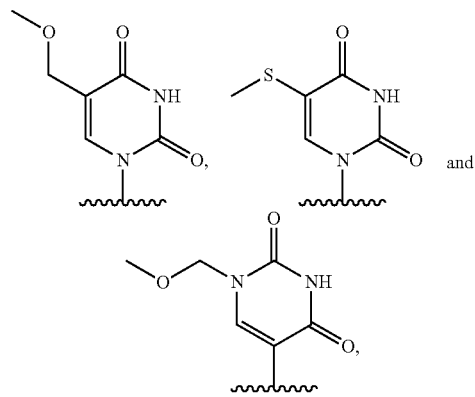

thereby inducing a mammalian cell to produce a recombinant protein.

In another embodiment, a modified mRNA of methods and compositions of the present invention is translated in the cell more efficiently than an unmodified mRNA molecule with the same sequence. In another embodiment, the modified mRNA molecule exhibits enhanced ability to be translated by a target cell. In another embodiment, translation is enhanced by a factor of 2-fold relative to its unmodified counterpart. In another embodiment, translation is enhanced by a 3-fold factor. In another embodiment, translation is enhanced by a 5-fold factor.

In another embodiment, translation is enhanced by a 7-fold factor. In another embodiment, translation is enhanced by a 10-fold factor. In another embodiment, translation is enhanced by a 15-fold factor. In another embodiment, translation is enhanced by a 20-fold factor. In another embodiment, translation is enhanced by a 50-fold factor. In another embodiment, translation is enhanced by a 100-fold factor. In another embodiment, translation is enhanced by a 200-fold factor. In another embodiment, translation is enhanced by a 500-fold factor. In another embodiment, translation is enhanced by a 1000-fold factor. In another embodiment, translation is enhanced by a 2000-fold factor. In another embodiment, the factor is 10-1000-fold. In another embodiment, the factor is 10-100-fold. In another embodiment, the factor is 10-200-fold. In another embodiment, the factor is 10-300-fold. In another embodiment, the factor is 10-500-fold. In another embodiment, the factor is 20-1000-fold. In another embodiment, the factor is 30-1000-fold. In another embodiment, the factor is 50-1000-fold. In another embodiment, the factor is 100-1000-fold. In another embodiment, the factor is 200-1000-fold. In another embodiment, translation is enhanced by any other significant amount or range of amounts. Each possibility represents a separate embodiment of the present invention.

Methods of determining translation efficiency are well known in the art, and include, e.g. measuring the activity of an encoded reporter protein (e.g luciferase or *renilla* or green fluorescent protein [Wall A A, Phillips A M et al, Effective translation of the second cistron in two *Drosophila* dicistronic transcripts is determined by the absence of in-frame AUG codons in the first cistron. J Biol Chem 2005; 280(30): 27670-8]), or measuring radioactive label incorporated into the translated protein (Ngosuwan J, Wang N M et al, Roles of cytosolic Hsp70 and Hsp40 molecular chaperones in post-translational translocation of presecretoiy proteins into the endoplasmic reticulum. J Biol Chem 2003; 278(9): 7034-42). Each method represents a separate embodiment of the present invention.

In another embodiment, the modified mRNA of methods and compositions of the present invention is significantly less immunogenic than an unmodified in vitro-synthesized mRNA molecule with the same sequence. In another embodiment, the modified mRNA molecule is 2-fold less immunogenic than its unmodified counterpart. In another embodiment, immunogenicity is reduced by a 3-fold factor. In another embodiment, immunogenicity is reduced by a 5-fold factor. In another embodiment, immunogenicity is reduced by a 7-fold factor. In another embodiment, immunogenicity is reduced by a 10-fold factor. In another embodiment, immunogenicity is reduced by a 15-fold factor. In another embodiment, immunogenicity is reduced by a fold factor. In another embodiment, immunogenicity is reduced by a 50-fold factor.

In another embodiment, immunogenicity is reduced by a 100-fold factor. In another embodiment, immunogenicity is reduced by a 200-fold factor. In another embodiment, immunogenicity is reduced by a 500-fold factor. In another embodiment, immunogenicity is reduced by a 1000-fold factor. In another embodiment, immunogenicity is reduced by a 2000-fold factor. In another embodiment, immunogenicity is reduced by another fold difference.

In another embodiment, "significantly less immunogenic" refers to a detectable decrease in immunogenicity. In another embodiment, the term refers to a fold decrease in immunogenicity (e.g. 1 of the fold decreases enumerated above). In another embodiment, the term refers to a decrease such that an effective amount of the modified mRNA can be administered without triggering a detectable immune response. In another embodiment, the term refers to a decrease such that the modified mRNA can be repeatedly administered without eliciting an immune response sufficient to detectably reduce expression of the recombinant protein. In another embodiment, the decrease is such that the modified mRNA can be repeatedly administered without eliciting an immune response sufficient to eliminate detectable expression of the recombinant protein.

"Effective amount" of the modified mRNA refers, in another embodiment, to an amount sufficient to exert a therapeutic effect. In another embodiment, the term refers to an amount sufficient to elicit expression of a detectable amount of the recombinant protein. Each possibility represents a separate embodiment of the present invention.

Reduced immunogenicity of the modified mRNA of the present invention is demonstrated herein. Methods of determining immunogenicity are well known in the art, and include, e.g. measuring secretion of cytokines (e.g. IL-12, IFN-α, TNF-α, RANTES, MIP-1α or β, IL-6, IFN-β, or IL-8; Examples herein), measuring expression of DC activation markers (e.g. CD83, HLA-DR, CD80 and CD86, Examples herein), or measuring ability to act as an adjuvant for an adaptive immune response. Each method represents a separate embodiment of the present invention. In another embodiment, the relative immunogenicity of the modified nucleotide and its unmodified counterpart are determined by determining the quantity of the modified nucleotide required to elicit one of the above responses to the same degree as a given quantity of the unmodified nucleotide. For example, if twice as much modified nucleotide is required to elicit the same response, than the modified nucleotide is two-fold less immunogenic than the unmodified nucleotide.

In another embodiment, the relative immunogenicity of the modified nucleotide and its unmodified counterpart are determined by determining the quantity of cytokine (e.g. IL-12, IFN-α, TNF-α, RANTES, MIP-1α or β, IL-6, IFN-β, or IL-8) secreted in response to administration of the modified nucleotide, relative to the same quantity of the unmodified nucleotide. For example, if one-half as much cytokine is secreted, than the modified nucleotide is two-fold less immunogenic than the unmodified nucleotide. In another embodiment, background levels of stimulation are subtracted before calculating the immunogenicity in the above methods. Each possibility represents a separate embodiment of the present invention.

In another embodiment, a method of present invention further comprises mixing the modified mRNA of the instant invention with a transfection reagent prior to the step of contacting. In another embodiment, a method of present invention further comprises administering the modified mRNA of the instant invention together with the transfection reagent. In another embodiment, the transfection reagent is a cationic lipid reagent.

In another embodiment, the transfection reagent is a lipid-based transfection reagent. In another embodiment, the transfection reagent is a protein-based transfection reagent. In another embodiment, the transfection reagent is a polyethyleneimine based transfection reagent. In another embodiment, the transfection reagent is calcium phosphate. In another embodiment, the transfection reagent is Lipofectin® or Lipofectamine®. In another embodiment, the transfection reagent is any other transfection reagent known in the art.

In another embodiment, the transfection reagent forms a liposome. Liposomes, in another embodiment, increase intracellular stability, increase uptake efficiency and improve biological activity.

In another embodiment, liposomes are hollow spherical vesicles composed of lipids arranged in a similar fashion as those lipids which make up the cell membrane. They have, in another embodiment, an internal aqueous space for entrapping water soluble compounds and range in size from 0.05 to several microns in diameter. In another embodiment, liposomes can deliver modified mRNA to cells in a biologically active form.

Each type of transfection reagent represents a separate embodiment of the present invention.

In another embodiment, the target cell of methods of the present invention is an antigen-presenting cell. In another embodiment, the cell is an animal cell. In another embodiment, the cell is a dendritic cell. In another embodiment, the cell is a neural cell. In another embodiment, the cell is a brain cell. In another embodiment, the cell is a spleen cell. In another embodiment, the cell is a lymphoid cell. In another embodiment, the cell is a lung cell. In another embodiment, the cell is a skin cell. In another embodiment, the cell is a keratinocyte. In another embodiment, the cell is an endothelial cell. In another embodiment, the cell is an astrocyte, a microglial cell, or a neuron. In another embodiment, the cell is an alveolar cell. In another embodiment, the cell is a surface alveolar cell. In another embodiment, the cell is an alveolar macrophage. In another embodiment, the cell is an alveolar pneumocyte. In another embodiment, the cell is a vascular endothelial cell. In another embodiment, the cell is a mesenchymal cell. In another embodiment, the cell is an epithelial cell. In another embodiment, the cell is a hematopoietic cell. In another embodiment, the cell is colonic epithelium cell. In another embodiment, the cell is a lung epithelium cell. In another embodiment, the cell is a bone marrow cell.

In other embodiments, the target cell is a Claudius' cell, Hensen cell, Merkel cell, Müller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, or zymogenic cell. Each possibility represents a separate embodiment of the present invention.

A variety of disorders may be treated by employing methods of the present invention including, inter alia, monogenic disorders, infectious diseases, acquired disorders, cancer, and the like. Exemplary monogenic disorders include ADA deficiency, cystic fibrosis, familial-hypercholesterolemia, hemophilia, chronic ganulomatous disease, Duchenne muscular dystrophy, Fanconi anemia, sickle-cell anemia, Gaucher's disease, Hunter syndrome, X-linked SCID, and the like. In another embodiment, the disorder treated involves one of the proteins listed supra. Each possibility represents a separate embodiment of the present invention. In another embodiment, the present invention provides a method for treating anemia in a subject, comprising contacting a cell of the subject with an in vitro-synthesized RNA molecule, the in vitro-synthesized RNA molecule encoding erythropoietin, thereby treating anemia in a subject.

In another embodiment, the in vitro-synthesized modified mRNA further comprises a modified nucleoside selected from the group consisting of:

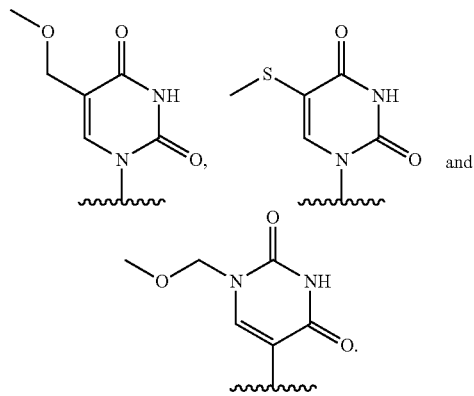

Each possibility represents a separate embodiment of the present invention. In another embodiment, the cell is a subcutaneous tissue cell.

In another embodiment, the cell is a lung cell. In another embodiment, the cell is a fibroblast. In another embodiment, the cell is a lymphocyte. In another embodiment, the cell is a smooth muscle cell. In another embodiment, the cell is any other type of cell known in the art. Each possibility represents a separate embodiment of the present invention.

In another embodiment, the present invention provides a method for treating a vasospasm in a subject, comprising contacting a cell of the subject with an in vitro-synthesized modified mRNA, the in vitro-synthesized modified mRNA encoding inducible nitric oxide synthase (iNOS), thereby treating a vasospasm in a subject.

In another embodiment, the present invention provides a method for improving a survival rate of a cell in a subject, comprising contacting the cell with an in vitro-synthesized modified mRNA, the in vitro-synthesized modified mRNA encodes a heat shock protein, thereby improving a survival rate of a cell in a subject.

In another embodiment, the cell whose survival rate is improved is an ischemic cell. In another embodiment, the cell is not ischemic. In another embodiment, the cell has been exposed to an ischemic environment. In another embodiment, the cell has been exposed to an environmental stress. Each possibility represents a separate embodiment of the present invention.

In another embodiment, the present invention provides a method for decreasing an incidence of a restenosis of a blood vessel following a procedure that enlarges the blood vessel, comprising contacting a cell of the blood vessel with an in vitro-synthesized modified mRNA, the in vitro-synthesized modified mRNA molecule encodes a heat shock protein, thereby decreasing an incidence of a restenosis in a subject.

In another embodiment, the procedure is an angioplasty. In another embodiment, the procedure is any other procedure known in the art that enlarges the blood vessel. Each possibility represents a separate embodiment of the present invention.

In another embodiment, the present invention provides a method for increasing a hair growth from a hair follicle is a scalp of a subject, comprising contacting a cell of the scalp with an in vitro-synthesized modified mRNA molecule, the in vitro-synthesized modified mRNA encodes a telomerase or an immunosuppressive protein, thereby increasing a hair growth from a hair follicle.

In another embodiment, the immunosuppressive protein is α-melanocyte-stimulating hormone (α-MSH). In another embodiment, the immunosuppressive protein is transforming growth factor-β1 (TGF-β1). In another embodiment, the immunosuppressive protein is insulin-like growth factor-I (IGF-I). In another embodiment, the immunosuppressive protein is any other immunosuppressive protein known in the art. Each possibility represents a separate embodiment of the present invention.

In another embodiment, the present invention provides a method of inducing expression of an enzyme with antioxidant activity in a cell, comprising contacting the cell with an in vitro-synthesized modified mRNA, the in vitro-synthesized modified mRNA encodes the enzyme, thereby inducing expression of an enzyme with antioxidant activity in a cell.

In another embodiment, the enzyme is catalase. In another embodiment, the enzyme is glutathione peroxidase. In another embodiment, the enzyme is phospholipid hydroperoxide glutathione peroxidase. In another embodiment, the enzyme is superoxide dismutase-1. In another embodiment, the enzyme is superoxide dismutase-2. In another embodiment, the enzyme is any other enzyme with antioxidant activity that is known in the art. Each possibility represents a separate embodiment of the present invention.

In another embodiment, the present invention provides a method for treating cystic fibrosis in a subject, comprising contacting a cell of the subject with an in vitro-synthesized modified mRNA, the in vitro-synthesized modified mRNA encodes Cystic Fibrosis Transmembrane Conductance Regulator (CFTR), thereby treating cystic fibrosis in a subject.

In another embodiment, the present invention provides a method for treating an X-linked agammaglobulinemia in a subject, comprising contacting a cell of the subject with an in vitro-synthesized modified mRNA, the in vitro-synthesized modified mRNA encodes a Bruton's tyrosine kinase, thereby treating an X-linked agammaglobulinemia.

In another embodiment, the present invention provides a method for treating an adenosine deaminase severe combined immunodeficiency (ADA SCID) in a subject, comprising contacting a cell of the subject with an in vitro-synthesized modified mRNA, the in vitro-synthesized modified mRNA encodes an ADA, thereby treating an ADA SCID.

In another embodiment, the present invention provides a method for reducing immune responsiveness of the skin and improve skin pathology, comprising contacting a cell of the subject with an in vitro-synthesized modified mRNA, the in vitro-synthesized modified mRNA encodes an ecto-nucleoside triphosphate diphosphydrolase, thereby reducing immune responsiveness of the skin and improve skin pathology.

In another embodiment, a modified mRNA of the present invention is encapsulated in a nanoparticle. Methods for nanoparticle packaging are well known in the art, and are described, for example, in Bose S, et al (Role of Nucleolin in Human Parainfluenza Virus Type 3 Infection of Human Lung Epithelial Cells. J. Virol. 78:8146. 2004); Dong Y et al. Poly(d,l-lactide-co-glycolide)/montmorillonite nanoparticles for oral delivery of anticancer drugs. Biomaterials 26:6068. 2005); Lobenberg R. et al (Improved body distribution of 14C-labelled AZT bound to nanoparticles in rats determined by radioluminography. J Drug Target 5:171.1998); Sakuma S R et al (Mucoadhesion of polystyrene nanoparticles having surface hydrophilic polymeric chains in the gastrointestinal tract. Int J Pharm 177:161. 1999); Virovic L et al. Novel delivery methods for treatment of viral hepatitis: an update. Expert Opin Drug Deliv 2:707.2005); and Zimmermann E et al, Electrolyte- and pH-stabilities of aqueous solid lipid nanoparticle (SLN) dispersions in artificial gastrointestinal media. Eur J Pharm Biopharm 52:203. 2001). Each method represents a separate embodiment of the present invention.

Various embodiments of dosage ranges of compounds of the present invention can be used in methods of the present invention. In one embodiment, the dosage is in the range of 1-10 μg/day. In another embodiment, the dosage is 2-10 μg/day. In another embodiment, the dosage is 3-10 μg/day. In another embodiment, the dosage is 5-10 μg/day. In another embodiment, the dosage is 2-20 μg/day. In another embodiment, the dosage is 3-20 μg/day. In another embodiment, the dosage is 5-20 μg/day. In another embodiment, the dosage is 10-20 μg/day. In another embodiment, the dosage is 3-40 μg/day. In another embodiment, the dosage is 5-40 μg/day. In another embodiment, the dosage is 10-40 μg/day. In another embodiment, the dosage is 20-40 μg/day. In another embodiment, the dosage is 5-50 μg/day. In another embodiment, the dosage is 10-50 μg/day. In another embodiment, the dosage is 20-50 μg/day. In one embodiment, the dosage is 1-100 μg/day. In another embodiment, the dosage is 2-100 μg/day. In another embodiment, the dosage is 3-100 μg/day. In another embodiment, the dosage is 5-100 μg/day. In another embodiment the dosage is 10-100 μg/day. In another embodiment the dosage is 20-100 μg/day. In another embodiment the dosage is 40-100 μg/day. In another embodiment the dosage is 60-100 μg/day.

In another embodiment, the dosage is 0.1 μg/day. In another embodiment, the dosage is 0.2 μg/day. In another embodiment, the dosage is 0.3 μg/day. In another embodiment, the dosage is 0.5 μg/day. In another embodiment, the dosage is 1 μg/day. In another embodiment, the dosage is 2 mg/day. In another embodiment, the dosage is 3 μg/day. In another embodiment, the dosage is 5 μg/day. In another embodiment, the dosage is 10 μg/day. In another embodiment, the dosage is 15 µg/day. In another embodiment, the dosage is 20 µg/day. In another embodiment, the dosage is 30 µg/day. In another embodiment, the dosage is 40 µg/day. In another embodiment, the dosage is 60 µg/day. In another embodiment, the dosage is 80 µg/day. In another embodiment, the dosage is 100 µg/day.

In another embodiment, the dosage is 10 µg/dose. In another embodiment, the dosage is 20 µg/dose. In another embodiment, the dosage is 30 µg/dose. In another embodiment, the dosage is 40 µg/dose. In another embodiment, the dosage is 60 µg/dose. In another embodiment, the dosage is 80 µg/dose. In another embodiment, the dosage is 100 µg/dose. In another embodiment, the dosage is 150 µg/dose. In another embodiment, the dosage is 200 µg/dose. In another embodiment, the dosage is 300 µg/dose. In another embodiment, the dosage is 400 µg/dose. In another embodiment, the dosage is 600 µg/dose. In another embodiment, the dosage is 800 µg/dose. In another embodiment, the dosage is 1000 µg/dose. In another embodiment, the dosage is 1.5 mg/dose. In another embodiment, the dosage is 2 mg/dose. In another embodiment, the dosage is 3 mg/dose. In another embodiment, the dosage is 5 mg/dose. In another embodiment, the dosage is 10 mg/dose. In another embodiment, the dosage is 15 mg/dose. In another embodiment, the dosage is 20 mg/dose. In another embodiment, the dosage is 30 mg/dose. In another embodiment, the dosage is 50 mg/dose. In another embodiment, the dosage is 80 mg/dose. In another embodiment, the dosage is 100 mg/dose.

In another embodiment, the dosage is 10-20 µg/dose. In another embodiment, the dosage is 20-30 µg/dose. In another embodiment, the dosage is 20-40 µg/dose. In another embodiment, the dosage is 30-60 µg/dose. In another embodiment, the dosage is 40-80 µg/dose. In another embodiment, the dosage is 50-100 µg/dose. In another embodiment, the dosage is 50-150 µg/dose. In another embodiment, the dosage is 100-200 µg/dose. In another embodiment, the dosage is 200-300 µg/dose. In another embodiment, the dosage is 300-400 µg/dose. In another embodiment, the dosage is 400-600 µg/dose. In another embodiment, the dosage is 500-800 µg/dose. In another embodiment, the dosage is 800-1000 µg/dose. In another embodiment, the dosage is 1000-1500 µg/dose. In another embodiment, the dosage is 1500-2000 µg/dose. In another embodiment, the dosage is 2-3 mg/dose. In another embodiment, the dosage is 2-5 mg/dose. In another embodiment, the dosage is 2-10 mg/dose. In another embodiment, the dosage is 2-20 mg/dose. In another embodiment, the dosage is 2-30 mg/dose. In another embodiment, the dosage is 2-50 mg/dose. In another embodiment, the dosage is 2-80 mg/dose.

In another embodiment, the dosage is 2-100 mg/dose. In another embodiment, the dosage is 3-10 mg/dose. In another embodiment, the dosage is 3-20 mg/dose. In another embodiment, the dosage is 3-30 mg/dose. In another embodiment, the dosage is 3-50 mg/dose. In another embodiment, the dosage is 3-80 mg/dose. In another embodiment, the dosage is 3-100 mg/dose. In another embodiment, the dosage is 5-10 mg/dose. In another embodiment, the dosage is 5-20 mg/dose. In another embodiment, the dosage is 5-30 mg/dose. In another embodiment, the dosage is 5-50 mg/dose. In another embodiment, the dosage is 5-80 mg/dose. In another embodiment, the dosage is 5-100 mg/dose. In another embodiment, the dosage is 10-20 mg/dose. In another embodiment, the dosage is 10-30 mg/dose. In another embodiment, the dosage is 10-50 mg/dose. In another embodiment, the dosage is 10-80 mg/dose. In another embodiment, the dosage is 10-100 mg/dose.

In another embodiment, the dosage is a daily dose. In another embodiment, the dosage is a weekly dose. In another embodiment, the dosage is a monthly dose. In another embodiment, the dosage is an annual dose. In another embodiment, the dose is one is a series of a defined number of doses. In another embodiment, the dose is a one-time dose. As described below, in another embodiment, an advantage of modified mRNA of the present invention is their greater potency, enabling the use of smaller doses.

In another embodiment, the present invention provides a method for producing a recombinant protein, comprising contacting an in vitro translation apparatus with an in vitro-transcribed modified mRNA of the present invention, the in vitro-transcribed modified mRNA comprises a modified nucleoside selected from the group consisting of:

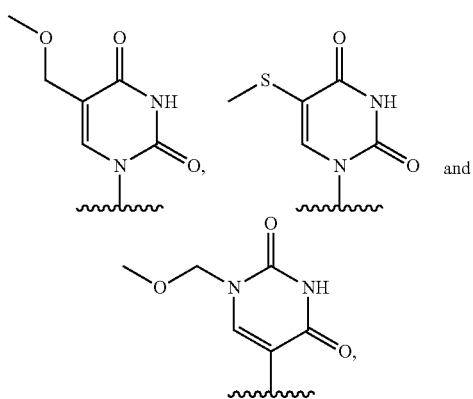

thereby producing a recombinant protein.

In another embodiment, the present invention provides an in vitro transcription apparatus, comprising a modified nucleoside selected from the group consisting of:

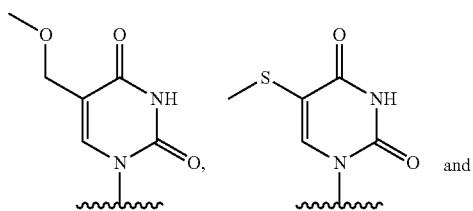

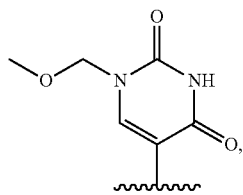

and a polymerase. In another embodiment, the present invention provides an in vitro transcription kit, comprising: a modified nucleoside selected from the group consisting of:

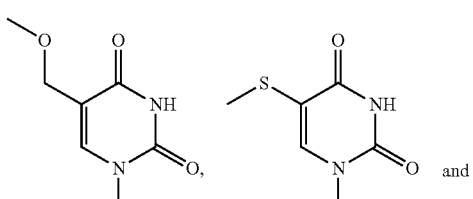

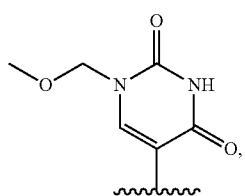

and a polymerase. Each possibility represents a separate embodiment of the present invention.

In another embodiment, the in vitro translation apparatus comprises a reticulocyte lysate. In another embodiment, the reticulocyte lysate is a rabbit reticulocyte lysate.

In another embodiment, the present invention provides a method of reducing an immunogenicity of an mRNA, the method comprising the step of replacing a nucleotide of the mRNA with a modified nucleotide comprising a modified nucleoside selected from the group consisting of:

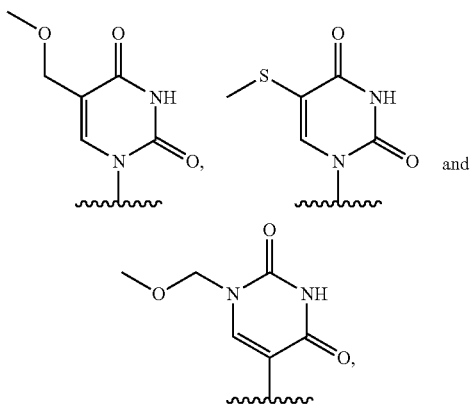

thereby reducing an immunogenicity of an mRNA.

In another embodiment, the present invention provides a method of reducing an immunogenicity of a gene-therapy vector comprising an mRNA molecule, the method comprising the step of replacing a nucleotide of the mRNA molecule with a modified nucleotide selected from the group consisting of:

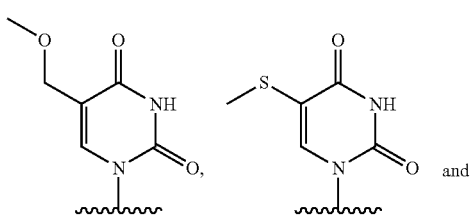

-continued

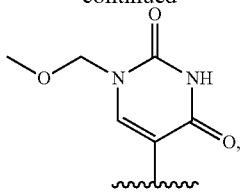

thereby reducing an immunogenicity of a gene-therapy vector.

In another embodiment, the present invention provides a method of enhancing in vitro translation from an mRNA molecule, the method comprising the step of replacing a nucleotide of the mRNA molecule with a modified nucleotide selected from the group consisting of:

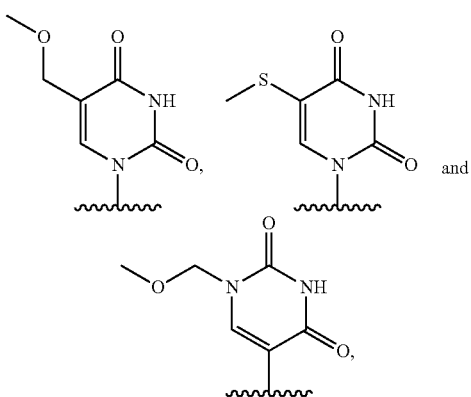

thereby enhancing in vitro translation from an oligoribo-nucleotide molecule or RNA molecule.

In another embodiment, the present invention provides a method of enhancing in vivo translation from a gene-therapy vector comprising an mRNA molecule, the method comprising the step of replacing a nucleotide of the mRNA molecule with a modified nucleotide selected from the group consisting of:

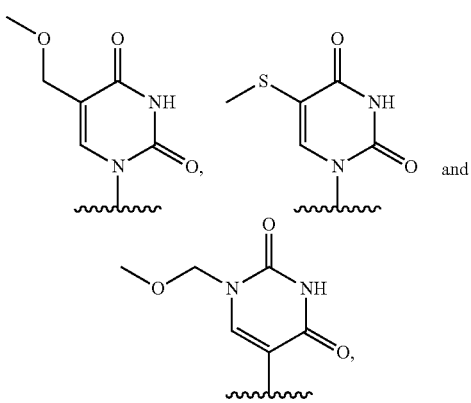

thereby enhancing in vivo translation from a gene-therapy vector.

In another embodiment, the present invention provides a method of increasing efficiency of delivery of a recombinant protein by a gene therapy vector comprising an mRNA molecule, the method comprising the step of replacing a nucleotide of the mRNA molecule with a modified nucleotide selected from the group consisting of:

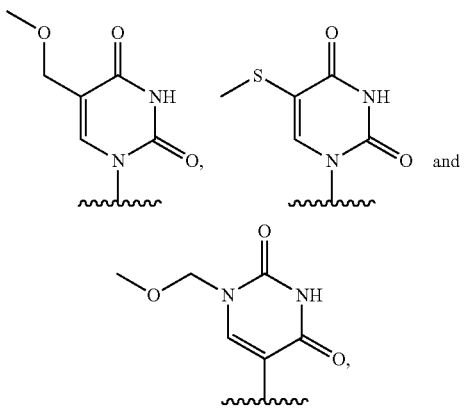

thereby increasing efficiency of delivery of a recombinant protein by a gene therapy vector.

In another embodiment, the present invention provides a method of increasing in vivo stability of gene therapy vector comprising an mRNA molecule, the method comprising the step of replacing a nucleotide of the mRNA molecule with a modified nucleotide selected from the group consisting of:

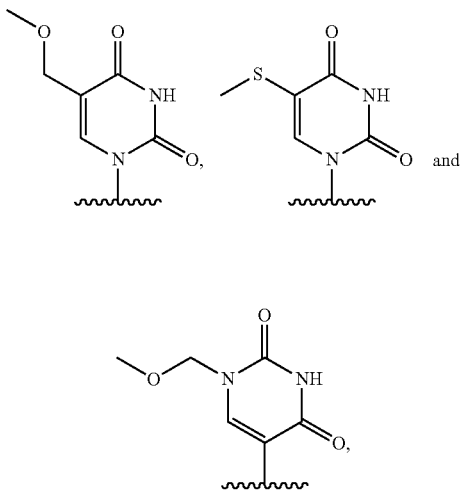

thereby increasing in vivo stability of gene therapy vector.

In another embodiment, the present invention provides a method of synthesizing an in vitro-transcribed modified mRNA comprising a modified nucleoside selected from the group consisting of:

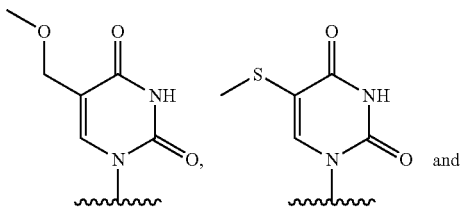

-continued

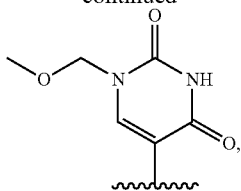

comprising contacting an isolated polymerase with a mixture of unmodified nucleotides and the modified nucleotide.

In another embodiment, in vitro transcription methods of the present invention utilize an extract from an animal cell. In another embodiment, the extract is from a reticulocyte or cell with similar efficiency of in vitro transcription. In another embodiment, the extract is from any other type of cell known in the art. Each possibility represents a separate embodiment of the present invention.

Any of the modified mRNA's of the present invention may be used, in another embodiment, in any of the methods of the present invention.

In another embodiment, the present invention provides a method of enhancing an immune response to an antigen, comprising administering the antigen in combination with mitochondrial (mt) modified mRNA.

In another embodiment, the present invention provides a method of reducing the ability of an mRNA molecule to stimulate a dendritic cell (DC), comprising modifying a nucleoside of the mRNA molecule by a method of the present invention.

In another embodiment, the DC is a DC1 cell. In another embodiment, the DC is a DC2 cell. In another embodiment, the DC is a subtype of a DC1 cell or DC2 cell. Each possibility represents a separate embodiment of the present invention.

In another embodiment, the present invention provides a method of reducing the ability of an mRNA molecule to stimulate signaling by TLR3, comprising modifying a nucleoside of the mRNA molecule by a method of the present invention. In another embodiment, the present invention provides a method of reducing the ability of an mRNA molecule to stimulate signaling by TLR7, comprising modifying a nucleoside of the mRNA molecule by a method of the present invention. In another embodiment, the present invention provides a method of reducing the ability of an mRNA molecule to stimulate signaling by TLR8 comprising modifying a nucleoside of the RNA molecule by a method of the present invention. Each possibility represents a separate embodiment of the present invention.

In another embodiment, all the inter-nucleotide linkages in the mRNA molecule are phosphodiester. In another embodiment, the inter-nucleotide linkages are predominantly phosphodiester. In another embodiment, most of the inter-nucleotide linkages are phosphorothioate. In another embodiment, most the inter-nucleotide linkages are phosphodiester. Each possibility represents a separate embodiment of the present invention. In another embodiment, the percentage of the inter-nucleotide linkages that are phosphodiester is above 50%. In another embodiment, the percentage is above 10%. In another embodiment, the percentage is above 15%. In another embodiment, the percentage is above 20%. In another embodiment, the percentage is above 25%. In another embodiment, the percentage is above 30%. In another embodiment, the percentage is above 35%. In another embodiment, the percentage is above 40%. In another embodiment, the percentage is above 45%. In another embodiment, the percentage is above 55%. In another embodiment, the percentage is above 60%. In another embodiment, the percentage is above 65%. In another embodiment, the percentage is above 70%. In another embodiment, the percentage is above 75%. In another embodiment, the percentage is above 80%. In another embodiment, the percentage is above 85%. In another embodiment, the percentage is above 90%. In another embodiment, the percentage is above 95%.

In another embodiment, a method of the present invention comprises increasing the number, percentage, or frequency of modified nucleosides in the modified mRNA to decrease immunogenicity or increase efficiency of translation. As provided herein, the number of modified residues in a modified mRNA determines, in another embodiment, the magnitude of the effects observed in the present invention.

In another embodiment, the present invention provides a method for introducing a recombinant protein into a cell of a subject, comprising contacting the subject with an in vitro-transcribed modified mRNA encoding the recombinant protein, the in vitro-transcribed modified mRNA molecule further comprising a modified nucleoside, thereby introducing a recombinant protein into a cell of a subject.

In another embodiment, the present invention provides a method for decreasing TNF-α production in response to a gene therapy vector in a subject, comprising the step of engineering the vector to contain a modified nucleoside selected from the group consisting of:

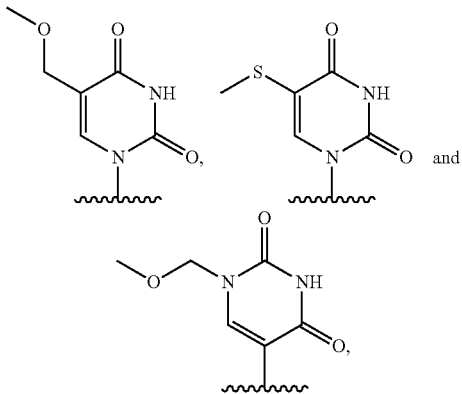

thereby decreasing TNF-α production in response to a gene therapy vector in a subject.

In another embodiment, the present invention provides a method for decreasing IL-12 production in response to a gene therapy vector in a subject, comprising the step of engineering the vector to contain a modified nucleoside selected from the group consisting of:

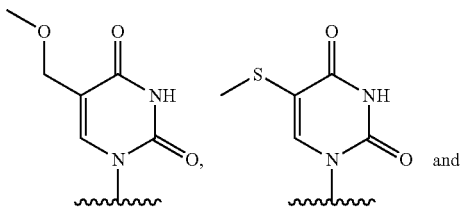

-continued

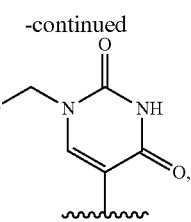

thereby decreasing IL-12 production in response to a gene therapy vector in a subject.

In another embodiment, the present invention provides a method of reducing an immunogenicity of a gene therapy vector, comprising introducing a modified nucleoside selected from the group consisting of:

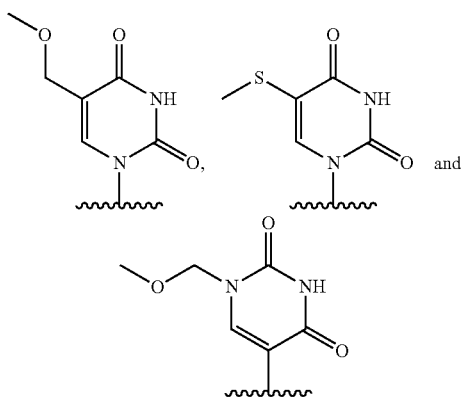

into said gene therapy vector, thereby reducing an immunogenicity of a gene therapy vector.

In another embodiment, an advantage of a modified mRNA of the present invention is that the modified mRNA does not incorporate to the genome (as opposed to DNA-based vectors). In another embodiment, an advantage is that translation of RNA, and therefore appearance of the encoded product, is instant. In another embodiment, an advantage is that the amount of protein generated from the mRNA can be regulated by delivering more or less RNA. In another embodiment, an advantage is that repeated delivery of unmodified RNA could induce autoimmune reactions.

In another embodiment, an advantage is lack of immunogenicity, enabling repeated delivery without generation of inflammatory cytokines.

In another embodiment, stability of RNA is increased by circularization, decreasing degradation by exonucleases.

In another embodiment, the present invention provides a method of treating a subject with a disease that comprises an immune response against a self-RNA molecule, comprising administering to the subject an antagonist of a TLR-3 molecule, thereby treating a subject with a disease that comprises an immune response against a self-RNA molecule.

In another embodiment, the present invention provides a method of treating a subject with a disease that comprises an immune response against a self-RNA molecule, comprising administering to the subject an antagonist of a TLR-7 molecule, thereby treating a subject with a disease that comprised an immune response against a self-RNA molecule.

In another embodiment, the present invention provides a method of treating a subject with a disease that comprises an immune response against a self-RNA molecule, comprising administering to the subject an antagonist of a TLR-8 molecule, thereby treating a subject with a disease that comprises an immune response against a self-RNA molecule.

In another embodiment, the disease that comprises an immune response against a self-RNA molecule is an autoimmune disease. In another embodiment, the disease is systemic lupus erythematosus (SLE). In another embodiment, the disease is another disease known in the art that comprises an immune response against a self-RNA molecule. Each possibility represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

In another embodiment, the present invention provides a kit for measuring or studying signaling by a TLR3, TLR7 and TLR8 receptor.

In another embodiment, a treatment protocol of the present invention is therapeutic. In another embodiment, the protocol is prophylactic. Each possibility represents a separate embodiment of the present invention.

In one embodiment, the phrase "contacting a cell" or "contacting a population" refers to a method of exposure, which can be direct or indirect. In one method such contact comprises direct injection of the cell through any means well known in the art, such as microinjection. In another embodiment, supply to the cell is indirect, such as via provision in a culture medium that surrounds the cell, or administration to a subject, or via any route known in the art. In another embodiment, the term "contacting" means that the molecule of the present invention is introduced into a subject receiving treatment, and the molecule is allowed to come in contact with the cell in vivo. Each possibility represents a separate embodiment of the present invention.

Methods for quantification of reticulocyte frequency and for measuring EPO biological activity are well known in the art, and are described, for Example, in Ramos, A S et al (Biological evaluation of recombinant human erythropoietin in pharmaceutical products. Braz J Med Biol Res 36:1561). Each method represents a separate embodiment of the present invention. Compositions of the present invention can be, in another embodiment, administered to a subject by any method known to a person skilled in the art, such as parenterally, paracancerally, transmucosally, transdermally, intramuscularly, intravenously, intra-dermally, subcutaneously, intra-peritoneally, intra-ventricularly, intra-cranially, intra-vaginally or intra-tumorally.

In another embodiment of methods and compositions of the present invention, the compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In other embodiments, the pharmaceutical compositions are administered by intravenous, intra-arterial, or intramuscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intramuscularly and are thus formulated in a form suitable for intramuscular administration.

In another embodiment, the pharmaceutical compositions are administered topically to body surfaces and are thus formulated in a form suitable for topical administration. Suitable topical formulations include gels, ointments, creams, lotions, drops and the like. For topical administration, the compositions or their physiologically tolerated derivatives are prepared and applied as solutions, suspensions, or emulsions in a physiologically acceptable diluent with or without a pharmaceutical carrier.

In another embodiment, the composition is administered as a suppository, for example a rectal suppository or a urethral suppository. In another embodiment, the pharmaceutical composition is administered by subcutaneous implantation of a pellet. In another embodiment, the pellet provides for controlled release of agent over a period of time.

In another embodiment, the active compound is delivered in a vesicle, e.g. a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be, in various embodiments, a solid carrier or diluent for solid formulations, a liquid carrier or diluent for liquid formulations, or mixtures thereof. In another embodiment, solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the compound is released over a period of time after administration. Controlled- or sustained-release compositions include formulation in lipophilic depots (e.g. fatty acids, waxes, oils). In another embodiment, the composition is an immediate-release composition, i.e. a composition in which the entire compound is released immediately after administration.

In another embodiment, molecules of the present invention are modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications also increase, in another embodiment, the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

An active component is, in another embodiment, formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Each of the above additives, excipients, formulations and methods of administration represents a separate embodiment of the present invention.

EXPERIMENTAL DETAILS SECTION

Example 1. Preparation of 5-methoxymethyluridine triphosphate

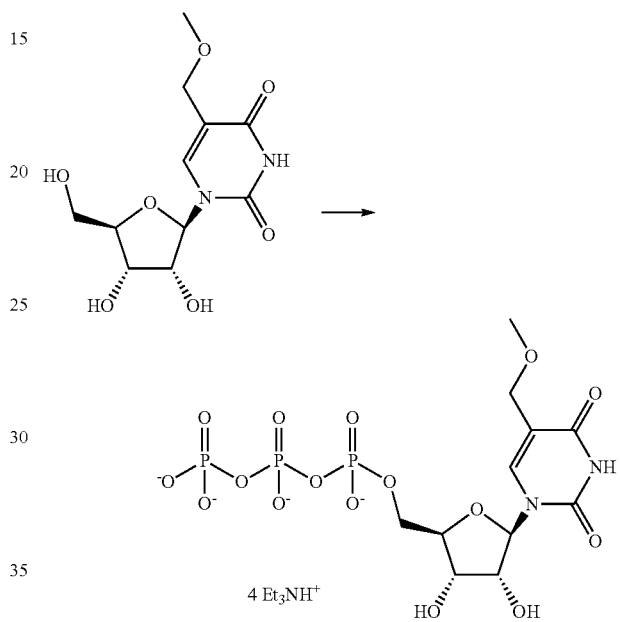

5-Methoxymethyluridine (35 mg, 0.12 mmol) (*Carbohydrate Research* 2011, 2136) was taken up in trimethyl phosphate (1.2 mL) and cooled to 0° C. Proton sponge (52 mg, 0.24 mmol) was added, and the mixture was stirred at 0° C. for 15 min. To this was added POCl$_3$ (28 µL, 0.309 mmol) dropwise. The mixture was stirred at 0° C. for 2.5 h. The mixture was cooled to −15° C., and DMF (0.8 mL) solution of tributylammonium pyrophosphate (466 mg, 0.850 mmol) and tributylamine (87 µL, 0.36 mmol) was added. The mixture was stirred at this temperature for 1 h 50 min and then added to 0.2 M (pH 8.5) aqueous triethylammonium bicarbonate (TEAB) (7 mL). The mixture was stirred at RT for 50 min and then freeze-dried by lyophilizer to give the crude product as semi-dry solid. This was taken up in acetonitrile (5 mL), MeOH (1 mL) and triethylamine (400 µL, 2.88 mmol) was added. The mixture was gently shaked for 5 min and concentrated. The residue was taken up in water and purified by HPLC (C18 column, 1-15% gradient MeCN in 0.1 M TEAB over 15 min; detection at 280 nm). Fractions containing the desired product were collected and lyophilized. The residue was again taken up in water and purified by ion-exchanged HPLC (Tosoh bioscience ltd, TSKgel DEAE-5 pW, 21.5 mm ID×15 cm; 2-100% gradient 1M aqueous TEAB buffer over 30 min. The other mobile phase is water; detection at 274 nm). Fractions containing the desired product were collected and lyophilized to give the product as white powder (29 mg). This compound was made into 100 mM aqueous solution for in vitro transcription study.

¹H NMR (400 MHz, CD₃OD) δ 8.10 (s, 1H), 5.97 (d, J=4 Hz, 1H), 4.44-4.10 (m, 7H), 3.34 (s, 3H), 3.05 (q, J=8 Hz, 24H), 1.25 (t, J=8 Hz, 36H); ³¹P NMR (162 MHz, CD₃OD—proton decoupled) δ −10.3 (d), −11.5 (d), −23.8 (t); Mass m/z 527 (M−1).

Example 2. Preparation of 5-methylthiouridine triphosphate

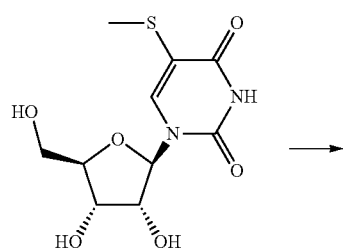

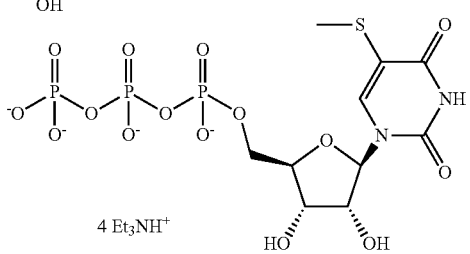

MAE679 was prepared in the same manner as MAY021 from 5-methylthiouridine (*Journal of heterocyclic chemistry* 1979, 16, 1049).
¹H NMR (400 MHz, D₂O) δ 7.85 (s, 1H), 5.92 (d, J=4 Hz, 1H), 4.42-4.35 (m, 2H), 4.25-4.09 (m, 3H), 3.13 (q, J=8 Hz, 24H), 2.27 (s, 3H), 1.21 (t, J=8 Hz, 36H); ³¹P NMR (162 MHz, D₂O—proton decoupled) δ −8.7 (br s), −11.6 (d), −22.9 (t); Mass m/z 529 (M−1).

Example 3. Preparation of 1-methoxymethylpseudouridine triphosphate

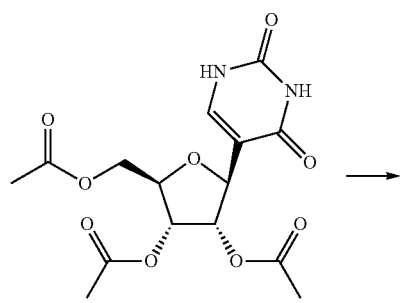

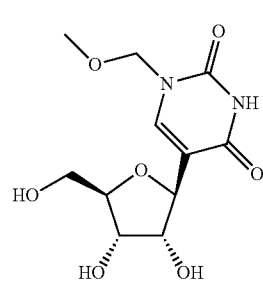

Methoxylmethyl chloride (30 µL, 0.40 mmol) was added to a solution of triacetoxy pseudouridine (130 mg, 0.351 mmol) (*Chemistry Letters* 2009, 38, 174) and diisopropylethylamine (72 µL, 0.41 mmol) in MeCN (4 mL) at −30° C. The mixture was warmed to 5° C. over 3 h, concentrated and purified by HPLC to give the product as an oil (110 mg). Mass m/z 415 (M+1). This was taken up in 2 M ammonia in methanol (5 mL, 10 mmol), and the mixture was stirred at RT for 46 h. The mixture was concentrated to give the crude product which was purified by SFC to give the product as a white solid (53 mg). ¹H NMR (400 MHz, CD₃OD) δ 7.81 (s, 1H), 5.12 (d, J=12 Hz, 1H), 5.09 (d, J=12 Hz, 1H), 4.62 (d, J=4 Hz, 1H), 4.17 (t, J=8 Hz, 1H), 4.07 (t, J=8 Hz, 1H), 3.95-3.91 (m, 1H), 3.81 (dd, J=12, 4 Hz, 1H), 3.66 (dd, J=12, 4 Hz, 1H), 3.37 (s, 3H); Mass m/z 289 (M+1).

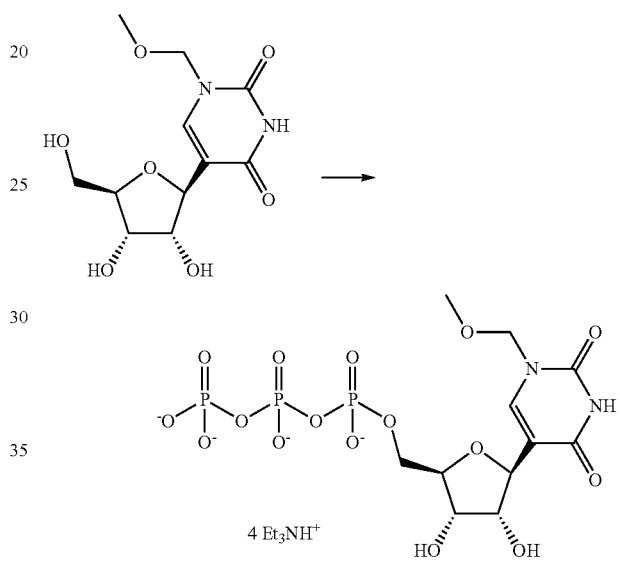

Example 3 was prepared in the same manner as Example from 1-methoxymethylpseudourdine.
¹H NMR (400 MHz, CD₃OD) δ 7.99 (s, 1H), 5.28 (d, J=8 Hz, 1H), 5.17 (d, J=8 Hz, 1H), 4.79-4.76 (m, 1H), 4.34-4.26 (m, 3H), 4.09-4.05 (m, 1H), 4.03-3.98 (m, 1H), 3.39 (s, 3H), 3.19 (q, J=8 Hz, 24H), 1.31 (t, J=8 Hz, 36H); ³¹P NMR (162 MHz, CD₃OD—proton decoupled) δ −10.2 (d), −11.2 (d), −23.7 (t); Mass m/z 527 (M−1).

Example 4. Preparation of 5-methoxycytidine triphosphate

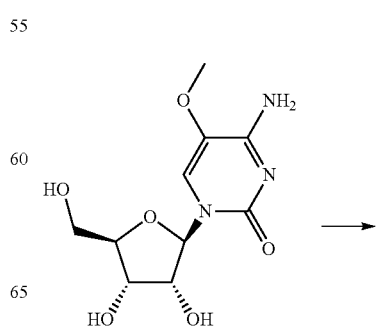

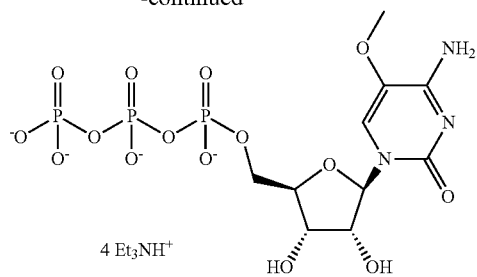

4 Et$_3$NH$^+$

MAL534 was prepared in the same manner as MAY021 from 5-methoxycytidine (*Journal of heterocyclic chemistry* 1972, 9(3), 545).

$^1$H NMR (400 MHz, CD$_3$OD) δ 7.59 (s, 1H), 6.01 (d, J=4 Hz, 1H), 4.44-4.35 (m, 2H), 4.31-4.22 (m, 2H), 4.15-4.11 (m, 1H), 4.03-3.98 (m, 1H), 3.90 (s, 3H), 3.11 (q, J=8 Hz, 24H), 1.27 (t, J=8 Hz, 36H); $^{31}$P NMR (162 MHz, CD$_3$OD—proton decoupled) δ −10.2 (d), −11.2 (d), −23.6 (t); Mass m/z 512 (M−1).

Example 5. In Vitro Transcription and Capping of Modified Synthetic mRNA

The modified synthetic mRNA was generated by in vitro transcription (IVT) incorporating the chemically modified nucleotide triphosphate (NTP) at 100% substitution of the corresponding natural nucleotide. The IVT plasmid template used contained a T7 promoter sequence and the human leptin coding sequence (Protein Accession #NP_000221) flanked by a 5' untranslated region (UTR) of Tobacco Etch Virus with a strong Kozak sequence, and 2 tandem copies of the human beta-globin 3'UTR (Holtkamp S et al. (2006) *Blood* 108: 4009-4017) followed by a poly-A tail comprising 120 nucleotides in length.

A typical in vitro transcription reaction was done using the following protocol:

| In vitro Transcription Reaction | |
|---|---|
| Reagent | Final concentration |
| Tris-HCl pH 8.0 | 40 mM |
| MgCl$_2$ | 20 mM |
| ATP, CTP, GTP, UTP for unmodified mRNA | 4 mM each |
| For modified mRNA, replace 100% ATP, CTP, GTP or UTP with 100% modified NTP | 4 mM |
| DTT | 10 mM |
| Spermidine | 2 mM |
| Linearized template plasmid DNA | 0.05 µg/µL |
| Pyrophosphatase | 0.004 U/µL |
| RNase inhibitor | 1 U/µL |
| T7 RNA polymerase | 5 U/µL |
| Nuclease-free water | to 100 µl total reaction volume |

The IVT reagents in the Table above were mixed and incubated for 1-2 hours at 37° C. The DNA template was then digested with 0.04 U/µL DNase (New England Biolabs), and incubated for 30 minutes at 37° C. The mRNA was precipitated by adding lithium chloride (LiCl) solution (Ambion, Cat. #AM9480) to a final concentration of 2.81 M and incubating for >1 hour at −20° C. The mixture was centrifuged at 20,000×g for 15 minutes at 4° C., and then the supernatant was removed and the pellet washed with 70% ethanol. After centrifugation for 10 minutes, the ethanol was removed and the pellet was resuspended in nuclease-free water. In cases where the mRNA is used for HPLC purification, a second precipitation was done by adding 10% volume of 3 M sodium acetate pH 5.5 and 1 volume of room temperature isopropanol followed by incubation overnight at −20° C. The mRNA was centrifuged, washed and resuspended as described above. mRNA concentration was quantified using the NanoDrop and analyzed using an Agilent 2100 Bioanalyzer to confirm proper size and quality (i.e. no degradation). The modified mRNA can then be stored at −80° C. until capping. IVT yields for modified mRNAs are shown as a percent of the unmodified mRNA yield.

The mRNA was enzymatically capped using a commercially available kit from New England Biolabs (Beverly Mass. USA). The mRNA and water mixture was heat denatured at 65° C. for 10 minutes, and then transferred to cold block to quench for 5 minutes. The stock solution of S-adenosyl methionine (SAM) (32 mM) was diluted 1:8 in water to 4 mM immediately before use, then the remaining reaction components were added in the order specified in the TABLE below. The mixture was incubated for 1 hour at 37° C. The sample was purified by LiCl precipitation as described above, and then stored at −80° C.

| Capping Reaction | | |
|---|---|---|
| Reagent | Stock concentration | Final concentration |
| mRNA (µg/µL) | | |
| Water | | |
| 10x Capping Buffer | 10x | 1x |
| GTP (mM) | 10 | 0.5 |
| SAM (mM) | 4 | 0.2 |
| RNase Inhibitor (U/µL) | 40 | 1 |
| Vaccinia capping enzyme (U/µL) | 10 | 0.5 |
| mRNA Cap 2'-O-Methyltransferase (U/µL) | 50 | 2.5 |

Example 6. Modified mRNA Transfection and In Vitro Translation

HEK293 cells were grown in Dulbecco's modified Eagle's medium supplemented with 10% fetal bovine serum in a 37° C. incubator with a humidified atmosphere of 5% CO$_2$. Prior to transfection, the cells were seeded at a density 5×10$^5$ cells per well in 6-well plates. The following day, 1.5 micrograms of capped unmodified or chemically modified leptin mRNA was complexed with Lipofectamine 2000 (Life Technologies) and transfected into cells according to the manufacturer's protocol. At 24 h post-transfection, secreted leptin protein concentration in the culture medium was measured by an Enzyme-linked immunosorbent assay (ELISA) using the Human Leptin Quantikine ELISA kit from R&D Systems (Minneapolis, Minn.). Protein expression levels for chemically modified mRNAs are shown as a percent of the unmodified mRNA level.

Example 7. In Vitro Immunogenicity Assay

To determine if the chemically modified mRNAs are immunogenic (e.g. induce a cellular innate immune response), the in vitro transcribed mRNAs were first purified by High performance liquid chromatography (HPLC) using a previously described method (Karikó K et al. (2011) *Nucleic Acids Res* 39(21): e142). Purification is done to remove contaminants from the in vitro transcribed mRNA (e.g. double-stranded RNA) that can induce type I interferons (IFN) and inflammatory cytokines.

The immunogenicity assay was done using human THP-1 monocyte cell line stably expressing an interferon regulatory factor (IRF)-inducible secreted embryonic alkaline phosphatase (SEAP) reporter construct (THP1-Blue™ ISG cells) from InvivoGen (San Diego, Calif.). This cell line is used to monitor activation of IFN signaling pathway as a measure of immunogenicity. Cells were grown in RPMI 1640 medium (Cat. #30-2001, ATCC) supplemented with 10% fetal bovine serum, 2 mM L-Glutamine, 100 µg/mL Normocin (InvivoGen), and 100 µg/mL Zeocin in a 37° C. incubator with a humidified atmosphere of 5% $CO_2$. To differentiate the monocytes into macrophage-like cells, the THP1-Blue™ ISG cells were seeded at 100,000 cells per well in 96-well plates and stimulated with 0.3 µM phorbol 12-myristate 13-acetate (PMA) for 3 hours, 4 days prior to transfection. 100 ng of capped unmodified or chemically modified mRNA was complexed with TransIT reagent (Cat. #MIR 2250, Mirus) in growth medium lacking antibiotics, and was then transfected into cells according to the manufacturer's protocol. Four hours later, the medium was removed and replaced with fresh growth medium without antibiotics. Cell culture supernatant was harvested after 19 hours and the level of IRF-induced SEAP activity was measured using InvivoGen's QUANTI-BLue™ assay with a spectrophotometer at 650 nm according to the manufacturer's protocol. All samples were evaluated in quadruplicate. The unmodified mRNA typically showed SEAP $OD_{650}$ values of 1.6 in this assay. Modified mRNA showing values less than the unmodified mRNA value are considered less immunogenic (i.e. elicit a reduced cellular innate immune response).

TABLE 1

Data Summary

| entry | Name of nucleosides with modified base | In vitro transcription (mRNA quantity relative to unmodified NTP in percentage) | In vitro translation (Protein quantity relative to unmodified mRNA in percentage) | In vitro Immunogenicity (SEAP OD 650 nm) |
|---|---|---|---|---|
| 1 | Unmodified | 100% | 100% | 1.6 |
| 2 | 5-dimethylaminouridine | <50% | n/a | n/a |
| 3 | 6-dimethylaminouridine | <50% | n/a | n/a |
| 4 | 5-acetamidouridine | <50% | <50% | n/a |
| 5 | 5-methoxycarbonyamino-uridine | >50% | <50% | n/a |
| 6 | 5-methylaminouridine | >50% | <50% | n/a |
| 7 | 5-isopropoxyuridine | <50% | <50% | n/a |
| 8 | 5-methylthiouridine | >50% | >50% | <0.5 |
| 9 | 5-methoxymethyluridine | >50% | >50% | <0.5 |
| 10 | 1-methyoxymethyl-pseudouridine | >50% | >50% | <0.5 |
| 11 | 1-methoxyethyl-pseudouridine | >50% | <50% | n/a |
| 12 | 5-hydroxymethylcytidine | >50% | >50% | >2 |
| 13 | 5-methoxycytidine | >50% | >50% | <0.5 |
| 14 | 1-((2R,3R,4S,5R)-3,4-dihydroxy-5-(hydroxymethyl)-tetrahydro-furan-2-yl)-6,7-dihydro-1H-cyclopenta[d]pyrimidine-2,4(3H,5H)-dione | <50% | n/a | n/a |
| 15 | 5-dimethylaminocytidine | >50% | <50% | <0.5 |
| 16 | 7-methyl-9-deazaguanosine | >50% | <50% | n/a |

The invention claimed is:

1. A modified messenger RNA comprising a modified nucleoside selected from the group consisting of:

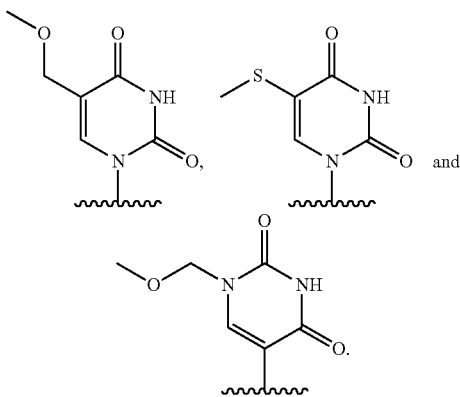

2. The modified messenger RNA of claim 1, wherein said modified messenger RNA further comprises a 5'-terminal cap comprising $N^7$-methylguanine and a poly-A tail.

3. The modified messenger RNA of claim 2, wherein the cap of the modified messenger RNA comprises $m^7$GpppG cap or 3'-O-methyl-$m^7$GpppG cap.

4. The modified messenger RNA of claim 1, wherein said RNA further comprises a cap-independent translational enhancer.

5. The modified messenger RNA of claim 1, wherein said RNA further comprises 5' and/or 3' untranslated regions (UTRs) that enhance translation.

6. The modified messenger RNA of claim 5, wherein said 5' and 3' UTRs comprise at least one UTR selected from the group consisting of a beta-globin 5' UTR, a tobacco etch virus (TEV) 5' UTR, and a beta-globin 3' UTR.

7. The modified messenger RNA of claim 1, wherein said modified messenger RNA is synthesized by in vitro transcription in a reaction mixture comprising a 5'-triphosphate derivative of a modified nucleoside selected from the group consisting of:

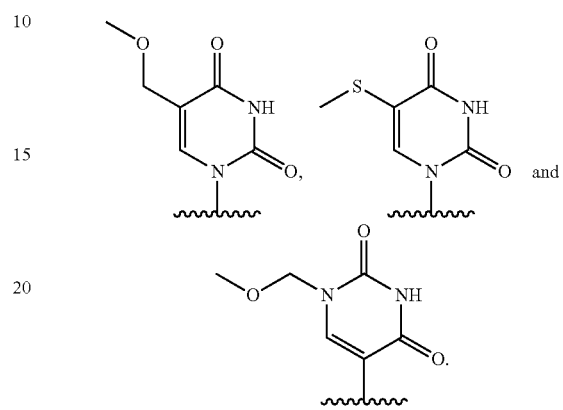

8. The modified messenger RNA of claim 1, wherein said modified messenger RNA further comprises a modified nucleoside selected from the group consisting of 5-methylcytidine ($m^5$C), pseudouridine ($\Psi$), 1-methypseudouridine ($m^1\Psi$), 5-methyluridine ($m^5$U), $N^6$-methyladenosine ($m^6$A), 2-thiouridine ($S^2$U) and 2'-O-methyluridine (2'-O-methyl-U).

* * * * *